United States Patent [19]

Borzatta et al.

[11] Patent Number: 5,310,767
[45] Date of Patent: May 10, 1994

[54] TETRAMETHYLPIPERIDINE COMPOUNDS FOR USE AS STABILIZERS FOR ORGANIC MATERIALS

[75] Inventors: Valerio Borzatta, Bologna; Graziano Vignali, Sasso Marconi, both of Italy

[73] Assignee: Ciba-Geigy Corporation, Ardsley, N.Y.

[21] Appl. No.: 988,503

[22] Filed: Dec. 10, 1992

[30] Foreign Application Priority Data

Dec. 17, 1991 [IT] Italy ............... MI 91 A 003374

[51] Int. Cl.$^5$ ............... C07D 401/12; C07D 401/14; C08K 5/34
[52] U.S. Cl. ................ 524/100; 524/96; 524/98; 540/460; 540/492; 544/113; 544/120; 544/123; 544/357; 544/408; 546/187; 252/401; 252/403
[58] Field of Search ........... 540/460, 492; 544/113, 544/120, 123, 357, 408; 546/187; 252/401, 403; 524/96, 98, 100, 103

[56] References Cited

U.S. PATENT DOCUMENTS

| | | | |
|---|---|---|---|
| 3,684,765 | 8/1972 | Matsui et al. | 524/103 |
| 3,904,581 | 9/1975 | Murayama et al. | 524/103 |
| 3,925,376 | 12/1975 | Chalmers et al. | 524/100 |
| 4,108,829 | 8/1978 | Cassandrini et al. | 544/198 |
| 4,279,804 | 7/1981 | Cantatore et al. | 546/186 |
| 4,316,025 | 2/1982 | Cantatore et al. | 544/364 |
| 4,433,145 | 2/1984 | Wiezer et al. | 544/198 |
| 4,533,688 | 8/1985 | Yoda et al. | 524/100 |
| 4,740,544 | 4/1988 | Nakahara et al. | 524/100 |
| 5,047,531 | 9/1991 | Cantatore et al. | 544/198 |
| 5,091,450 | 2/1992 | Borzatta et al. | 544/198 |
| 5,102,927 | 4/1992 | Rody et al. | 524/100 |
| 5,187,275 | 2/1993 | Borzatta et al. | 549/198 |
| 5,198,546 | 3/1993 | Borzatta et al. | 544/198 |

FOREIGN PATENT DOCUMENTS

| | | |
|---|---|---|
| 0019578 | 11/1980 | European Pat. Off. . |
| 0117229 | 8/1984 | European Pat. Off. . |
| 0176106 | 4/1986 | European Pat. Off. . |
| 0227640 | 7/1987 | European Pat. Off. . |
| 0410934 | 1/1991 | European Pat. Off. . |
| 0491659 | 6/1992 | European Pat. Off. . |
| 2027023 | 2/1980 | United Kingdom . |

*Primary Examiner*—Kriellion S. Morgan
*Attorney, Agent, or Firm*—Luther A. R. Hall

[57] ABSTRACT

The present invention relates to novel tetramethylpiperidine compounds of the formula (I)

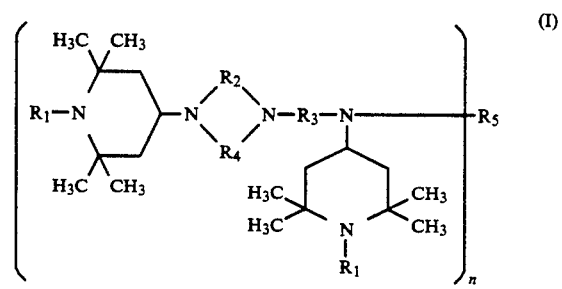

in which $R_1$ is e.g. hydrogen or methyl, $R_2$ and $R_3$ are e.g. —$(CH_2)_2$—, $R_4$ is e.g. —CO—, —COCO— or —COCH$_2$CO—, n is e.g. 1 and $R_5$ is e.g. hydrogen or allyl.

These compounds are suitable for use as light stabilizers, heat stabilizers and oxidation stabilizers for organic materials.

14 Claims, No Drawings

TETRAMETHYLPIPERIDINE COMPOUNDS FOR USE AS STABILIZERS FOR ORGANIC MATERIALS

The present invention relates to novel piperidine compounds, to their use as light stabilisers, heat stabilisers and oxidation stabilisers for organic materials, in particular synthetic polymers, and to the materials thus stabilised.

The stabilisation of synthetic polymers with derivatives of 2,2,6,6-tetramethylpiperidine has been described in numerous patents, in particular in U.S. Pat. Nos. 3,684,765, 3,904,581, 3,925,376, 4,108,829, 4,279,804, 4,316,025, 4,433,145, 4,533,688 and 4,740,544 and in European Laid Open Prints 117 229, 176 106, 227 640, 410 934 and 491 659.

The present invention relates to novel compounds of the formula (I)

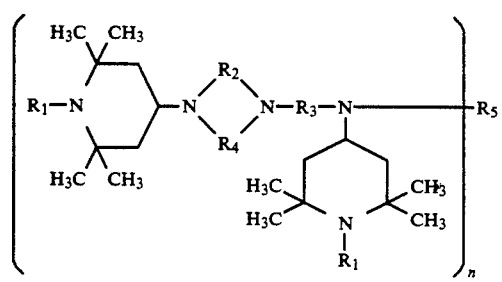
(I)

in which $R_1$ is hydrogen, $C_1$–$C_8$alkyl, O, OH, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl; or $C_1$–$C_8$acyl, $R_2$ and $R_3$ which can be identical or different are $C_2$–$C_3$alkylene, $R_4$ is —CO—, —COCO— or —COCH$_2$CO— n is 1, 2, 3 or 4, and, when n is 1, $R_5$ is hydrogen, $C_1$–$C_{18}$alkyl, $C_3$–$C_6$alkenyl, $C_7$–$C_9$phenylalkyl which is unsubstituted or mono-, di- or tri-substituted on the phenyl by $C_1$–$C_4$alkyl; or $R_5$ is one of the groups of the formulae (IIa)–(IIc)

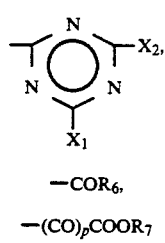
(IIa)

—COR$_6$, (IIb)

—(CO)$_p$COOR$_7$ (IIc)

in which $X_1$ and $X_2$ which can be identical or different are a group —OR$_8$, —SR$_8$ or

where $R_8$, $R_9$ and $R_{10}$ which can be identical or different are hydrogen, $C_1$–$C_{18}$alkyl, $C_5$–$C_{12}$cycloaklyl which is unsubstituted or mono-, di- or tri-substituted by $C_1$–$C_4$alkyl; $C_3$–$C_{18}$alkenyl, phenyl which is unsubstituted or mono-, di- or tri-substituted by $C_1$–$C_4$alkyl or $C_1$–$C_4$alkoxy; $C_7$–$C_9$phenylalkyl which is unsubstituted or mono-, di- or tri-substituted on the phenyl by $C_1$–$C_4$alkyl; $C_2$–$C_4$alkyl substituted in the 2-, 3- or 4-position by OH, by $C_1$–$C_8$alkoxy, by di($C_1$–$C_4$alkyl)amino or by a nitrogen-containing 5-to 7-membered heterocyclic group with the free valency on the nitrogen atom; tetrahydrofurfuryl or a group of the formula (III)

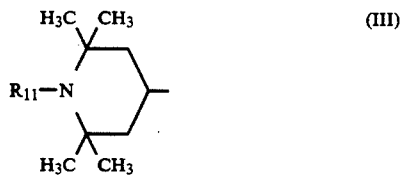
(III)

where $R_{11}$ is as defined for $R_1$, or

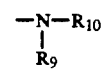

is a 5- to 7-membered heterocyclic group, or $X_1$ and $X_2$ are one of the groups of the formulae (IVa)–(IVd)

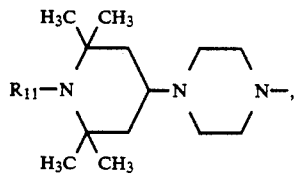
(IVa)

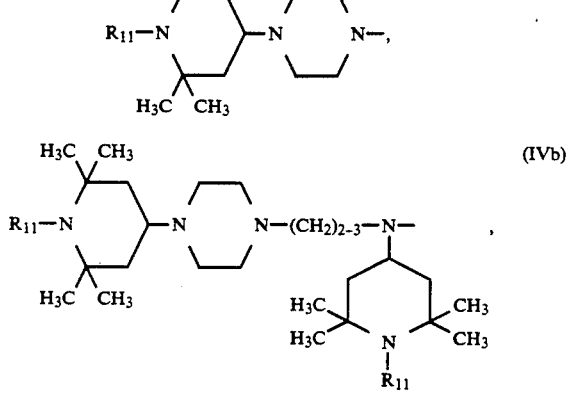
(IVb)

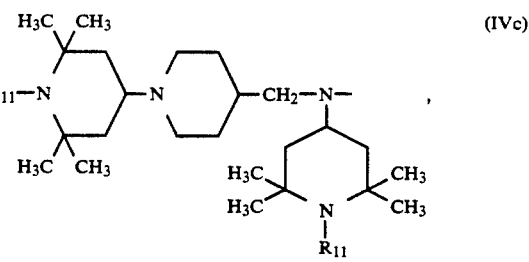
(IVc)

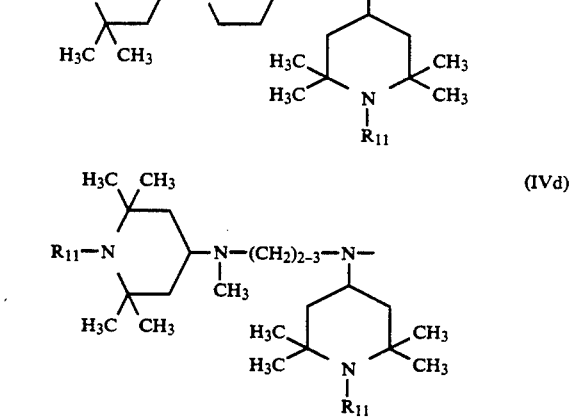
(IVd)

with $R_{11}$ as defined above, $R_6$ is hydrogen, $C_1$–$C_{18}$alkyl, $C_5$–$C_{12}$cycloalkyl which is unsubstituted or mono-, di- or tri-substituted by $C_1$–$C_4$alkyl; $C_2$–$C_{18}$alkenyl, phenyl which is unsubstituted or mono-, di- or tri-substituted by $C_1$–$C_4$alkyl or $C_1$–$C_4$alkoxy and/or by an OH group; $C_7$–$C_9$phenylalkyl which is unsubstituted or mono-, dior tri-substituted on the phenyl by $C_1-C_4$alkyl and/or an OH group; p is zero or 1, and $R_7$ is $C_1-C_{18}$alkyl, $C_5-C_{12}$cycloalkyl which is unsubstituted or mono-, di- or tri-substituted by $C_1-C_4$alkyl; $C_3-C_{18}$alkenyl, $C_7-C_9$-phenylalkyl which is unsubstituted or mono-, di- or tri-substituted on the phenyl by $C_1-C_4$alkyl; or a group of the formula (III), and, when n is 2, $R_5$ is $C_2-C_{12}$alkylene, $C_4-C_{12}$alkylene interrupted by 1, 2 or 3 oxygen atoms; 2-hydroxytrimethylene, phenylenedimethylene or one of the groups of the formulae (Va)–(Ve)

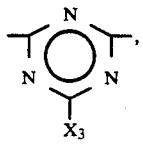 (Va)

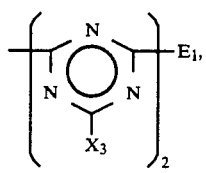 (Vb)

$-CO-R_{12}-CO-$, (Vc)

$-COO-R_{13}-OOC-$, (Vd)

$-(CH_2)_qCO-$ (Ve)

in which $X_3$ is as defined above for $X_1$ and $X_2$ or is a group of the formula (VI)

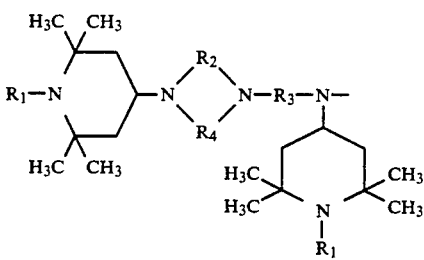 (VI)

where $R_1$, $R_2$, $R_3$ and $R_4$ are as defined above, $E_1$ is one of the groups of the formulae (VIIa)–(VIIc)

$-G_1-R_{14}-G_2-$, (VIIa)

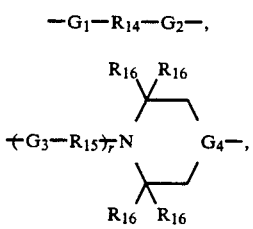 (VIIb)

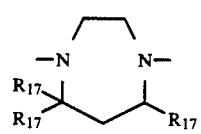 (VIIc)

in which $G_1$, $G_2$ and $G_3$ which can be identical or different are $-O-$ or

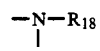

where $R_{18}$ is hydrogen, $C_1-C_{18}$alkyl, $C_5-C_{12}$cycloalkyl which is unsubstituted or mono-, di- or tri-substituted by $C_1-C_4$alkyl; $C_7-C_9$phenylalkyl which is unsubstituted or mono-, di- or tri-substituted on the phenyl by $C_1-C_4$alkyl; or a group of the formula (III), $R_{14}$ is $C_2-C_{12}$alkylene, $C_4-C_{12}$alkylene interrupted by 1, 2 or 3 oxygen atoms or by 1 or 2

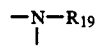

groups where $R_{19}$ is as defined above for $R_{18}$ or is $C_1-C_8$acyl or $(C_1-C_8$alkoxy)carbonyl; or $R_{14}$ is further $C_5-C_7$cycloalkylene unsubstituted or substituted by $C_1-C_4$alkyl; $C_5-C_7$cycloalkylenedi($C_1-C_4$alkylene), $C_1-C_4$alkylenedi($C_5-C_7$cycloalkylene), $C_2-C_4$alkylidenedi($C_5-C_7$cycloalkylene), phenylene unsubstituted or substituted by $C_1-C_4$alkyl; phenylenedi($C_1-C_4$alkylene), $C_1-C_4$alkylenediphenylene or $C_2-C_4$alkylidenediphenylene, $R_{15}$ is $C_2-C_6$alkylene, $G_4$ is one of the groups $>N-(R_{15}-G_3)_s$, $>CH-O-$ or

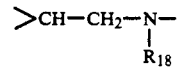

with $R_{18}$ as defined above, r and s which can be identical or different are zero or 1, $R_{16}$ is hydrogen or can also be methyl when r is 1 and $G_4$ is $>CH-O-$, and $R_{17}$ is hydrogen or methyl, $R_{12}$ is a direct bond, $C_1-C_{12}$alkylene, $C_2-C_4$alkenylene, cyclohexylene, cyclohexenylene or phenylene, $R_{13}$ is $C_2-C_{12}$alkylene, $C_4-C_{12}$alkylene interrupted by 1, 2 or 3 oxygen atoms, $C_5-C_7$cycloalkylene unsubstituted or substituted by $C_1-C_4$alkyl; $C_5-C_7$cycloalkylenedi($C_1-C_4$alkylene) or $C_2-C_4$alkylidenedi($C_5-C_7$cycloalkylene) and q is zero or an integer from 1 to 10, and when n is 3, $R_5$ is aliphatic $C_4-C_{18}$ triacyl, aromatic $C_9-C_{18}$triacyl or a group of the formula (VIII)

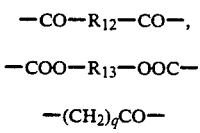 (VIII)

in which $X_3$ is as defined above and $E_2$ is one of the groups of the formula (IXa)–(IXc)

$-G_5-R_{20}-N-R_{21}-G_6-$, (IXa)

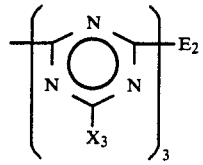

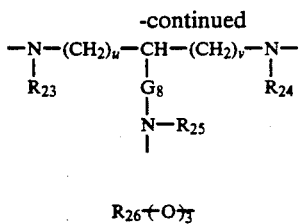 (IXb)

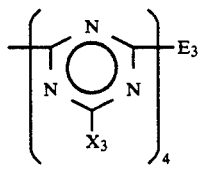 (IXc)

in which $G_5$, $G_6$ and $G_7$ which can be identical or different are as defined above for $G_1$, $G_2$ and $G_3$; $R_{20}$, $R_{21}$ and $R_{22}$ which can be identical or different are $C_2$-$C_6$alkylene, t is zero or 1, $R_{23}$, $R_{24}$ and $R_{25}$ which can be identical or different are as defined above for $R_{18}$; $G_8$ is a direct bond or —$CH_2$—, u and v which can be identical or different are integers from 2 to 6 and $R_{26}$ is $C_3$-$C_{12}$alkanetriyl, and, when n is 4, $R_5$ is aliphatic $C_6$-$C_{18}$tetraacyl, aromatic $C_{10}$-$C_{18}$tetraacyl, tetrahydrofuran-2,3,4,5-tetracarbonyl or a group of the formula (X)

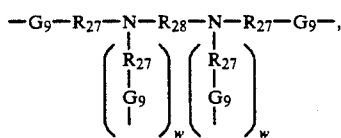 (X)

in which $X_3$ is as defined above and $E_3$ is one of the groups of the formulae (XIa)-(XIc)

 (XIa)

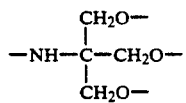

$R_{29}$—(—O—)$_{\overline{w}}$, (XIb)

$$\begin{array}{c} CH_2O- \\ | \\ -NH-C-CH_2O- \\ | \\ CH_2O- \end{array}$$ (XIc)

in which $G_9$ is as defined above for $G_1$, $G_2$ and $G_3$; $R_{27}$ and $R_{28}$ which can be identical or different are $C_2$-$C_6$alkylene, w is zero or 1 and $R_{29}$ is $C_4$-$C_{12}$alkanetetrayl.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of OH-substituted $C_2$-$C_4$alkyl are 2-hydroxyethyl, 2-hydroxypropyl, 3-hydroxypropyl, 2-hydroxybutyl and 4-hydroxybutyl. 2-Hydroxyethyl is preferred.

Examples of $C_2$-$C_4$alkyl substituted by $C_1$-$C_8$alkoxy, preferably $C_1$-$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di($C_1$-$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Examples of $C_2$-$C_4$alkyl substituted by a nitrogen-containing 5- to 7-membered heterocyclic group are groups of the formula

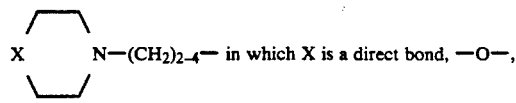 in which X is a direct bond, —O—, —CH$_3$N—, —CH$_2$— or —CH$_2$CH$_2$—.

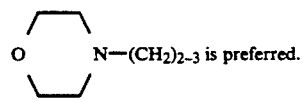 is preferred.

Examples of alkoxy having not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$Alkoxy, in particular heptoxy or octoxy, is preferred for $R_1$ and $R_{11}$.

Examples of substituted or unsubstituted $C_5$-$C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl which is unsubstituted or substituted by $C_1$-$C_4$alkyl is preferred.

Representative examples of $C_5$-$C_{12}$cycloalkoxy $R_1$ and $R_{11}$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having not more than 18 carbon atoms are vinyl, allyl, 2-methylallyl, butenyl, hexenyl, decenyl, undecenyl, heptadecenyl and oleyl. When $R_1$ and $R_{11}$ are $C_3$-$C_6$alkenyl, the carbon atom in the 1 position is preferably saturated.

Examples of substituted phenyl are methylphenyl, dimethylphenyl, trimethylphenyl, t-butylphenyl, di-t-butylphenyl, 3,5-di-t-butyl-4-methylphenyl, methoxyphenyl, ethoxyphenyl, hydroxyphenyl and 3,5-di-t-butyl-4-hydroxyphenyl.

Examples of $C_7$-$C_9$phenylalkyl which is unsubstituted or substituted on the phenyl are benzyl, methylbenzyl, dimethylbenzyl, trimethylbenzyl, t-butylbenzyl, 2-phenylethyl and 2-(3,5-di-t-butyl-4-hydroxyphenyl)ethyl.

Acyl $R_1$, $R_{11}$ and $R_{19}$ having not more than 8 carbon atoms can be an aliphatic or aromatic group. Representative examples are formyl, acetyl, propionyl, butyryl, pentanoyl, hexanoyl, heptanoyl, octanoyl, benzoyl, acryloyl or crotonyl. $C_1$-$C_8$alkanoyl, $C_3$-$C_8$alkenoyl and benzoyl are preferred. Acetyl is especially preferred.

Representative examples of a 5- to 7-membered heterocyclic group

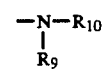

are 1-pyrrolidyl, 1-piperidyl, 4-morpholinyl, 4-methyl-1-piperazinyl and 1-hexahydroazepinyl. 4-Morpholinyl is preferred.

Examples of alkylene having not more than 12 carbon atoms are methylene, ethylene, propylene, trimethylene, tetramethylene, pentamethylene, 2,2-dimethyltrimethylene, hexamethylene, trimethylhexamethylene, decamethylene and dodecamethylene.

Examples of $C_4$–$C_{12}$alkylene interrupted by 1, 2 or 3 oxygen atoms are 3-oxapentane-1,5-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Preferred examples of $C_4$–$C_{12}$alkylene $R_{14}$ interrupted by 1 or 2

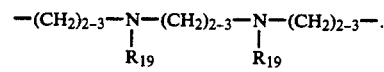

groups are the groups —$(CH_2)_{2-6}$—N($R_{19}$)—$(CH_2)_{2-6}$— and

—$(CH_2)_{2-3}$—N($R_{19}$)—$(CH_2)_{2-3}$—N($R_{19}$)—$(CH_2)_{2-3}$—.

Representative examples of groups containing 1 or 2 $C_5$–$C_7$cycloalkylene groups are cyclohexylene, methylcyclohexylene, cyclohexylenedimethylene, methylenedicyclohexylene and isopropylidenedicyclohexylene.

Representative examples of groups containing 1 or 2 phenylene groups are phenylene, methylphenylene, dimethylphenylene, phenylenedimethylene, methylenediphenylene and isopropylidenediphenylene.

Examples of $C_2$–$C_4$alkenylene are vinylene, methylvinylene and dimethylvinylene.

Aliphatic $C_4$–$C_{18}$triacyl $R_5$ can be unsubstituted or substituted by an OH group. Preferred examples are the triacyl derivatives of methanetricarboxylic, 1,1,2-ethanetricarboxylic, 1,2,3-propanetricarboxylic, citric or 1,2,3-butanetricarboxylic acid.

Aromatic $C_9$–$C_{18}$triacyl $R_5$ is, for example, a triacyl derivative of 1,2,4-benzenetricarboxylic or 1,3,5-benzenetricarboxylic acid.

Preferred examples of $C_3$–$C_{12}$alkanetriyl $R_{26}$ are 1,2,3-propanetriyl, 1,2,4-butanetriyl, 1,2,6-hexanetriyl or a group

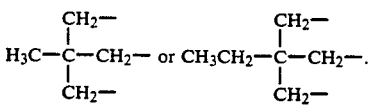

Aliphatic $C_6$–$C_{18}$tetraacyl $R_5$ is, for example, a tetraacyl derivative of 1,1,3,3-propanetetracarboxylic acid or 1,2,3,4-butanetetracarboxylic acid.

Aromatic $C_{10}$–$C_{18}$tetraacyl $R_5$ is, for example, a tetraacyl derivative of 1,2,4,5-benzenetetracarboxylic acid.

Preferred examples of $C_4$–$C_{12}$alkanetetrayl $R_{29}$ are 1,2,3,4-butanetetrayl and the group

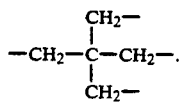

$(C_1$–$C_8$alkoxy)carbonyl is for example methoxycarbonyl, ethoxycarbonyl, propoxycarbonyl, butoxycarbonyl, pentoxycarbonyl, hexoxycarbonyl, heptoxycarbonyl or octoxycarbonyl.

The preferred definitions of $R_1$ and $R_{11}$ are hydrogen, $C_1$–$C_4$alkyl, OH, $C_6$–$C_{12}$alkoxy, $C_5$–$C_8$cycloalkoxy, allyl, benzyl or acetyl, in particular hydrogen or methyl.

Those compounds of the formula (I) are preferred in which $R_2$ and $R_3$ which can be identical or different are $C_2$–$C_3$alkylene, $R_4$ is —CO—, —COCO— or —COCH$_2$CO—, n is 1, 2, 3 or 4 and, when n is 1, $R_5$ is hydrogen, $C_1$–$C_{18}$alkyl, $C_3$–$C_4$alkenyl, benzyl which is unsubstituted or mono-, di- or tri-substituted on the phenyl by $C_1$–$C_4$alkyl; or $R_5$ is one of the groups of the formulae (IIa)–(IIc) in which $X_1$ and $X_2$ which can be identical or different are a group —$OR_8$, —$SR_8$ or

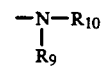

where $R_8$, $R_9$ and $R_{10}$ which can be identical or different are hydrogen, $C_1$–$C_{18}$alkyl, $C_5$–$C_8$cycloalkyl which is unsubstituted or mono-, di- or tri-substituted by $C_1$–$C_4$alkyl; $C_3$–$C_{18}$alkenyl, phenyl which is unsubstituted or mono-, di- or tri-substituted by $C_1$–$C_4$alkyl or $C_1$–$C_4$alkoxy; benzyl which is unsubstituted or mono-, di- or tri-substituted on the phenyl by $C_1$–$C_4$alkyl; $C_2$–$C_3$alkyl substituted in the 2- or 3-position by OH, by $C_1$–$C_4$alkoxy, by di($C_1$–$C_4$alkyl)amino or by a group

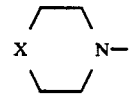

where X is a direct bond, —O—, —$CH_2$— or —$CH_2CH_2$—; tetrahydrofurfuryl or a group of the formula (III), or the group

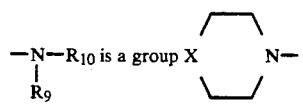

as defined above, or $X_1$ and $X_2$ are one of the groups of the formulae (IVa)–(IVd), $R_6$ is hydrogen, $C_1$–$C_{17}$alkyl, $C_5$–$C_8$cycloalkyl which is unsubstituted or mono-, di- or tri-substituted by $C_1$–$C_4$alkyl; $C_2$–$C_{17}$alkenyl, phenyl which is unsubstituted or mono-, di- or tri-substituted by $C_1$–$C_4$alkyl or $C_1$–$C_4$alkoxy and/or an OH group; benzyl or phenylethyl which both are unsubstituted or mono-, di- or tri-substituted on the phenyl by $C_1$–$C_4$alkyl and/or an OH group; p is zero or 1, $R_7$ is $C_1$–$C_{18}$alkyl, $C_5$–$C_8$cycloalkyl which is mono-, di- or tri-substituted by $C_1$–$C_4$alkyl; $C_3$–$C_{18}$alkenyl, benzyl which is unsubstituted or mono-, di- or trisubstituted on the phenyl by $C_1$–$C_4$alkyl; or a group of the formula (III), and, when n is 2, $R_5$ is $C_2$–$C_{10}$alkylene, $C_4$–$C_{10}$alkylene interrupted by 1, 2 or 3 oxygen atoms; 2-hydroxytrimethylene, phenylenedimethylene or one of the groups of the formulae (Va)–(Ve) in which $X_3$ is as defined above for $X_1$ and $X_2$ or is a group of the formula (VI), $E_1$ is one of the groups of the formulae (VIIa)–(VIIc) in which $G_1$, $G_2$ and $G_3$ which can be identical or different are —O— or

where $R_{18}$ is hydrogen, $C_1$-$C_{18}$alkyl, $C_5$-$C_8$cycloalkyl which is unsubstituted or mono-, di- or tri-substituted by $C_1$-$C_4$alkyl; benzyl which is unsubstituted or mono-, di- or tri-substituted on the phenyl by $C_1$-$C_4$alkyl; or a group of the formula (III), $R_{14}$ is $C_2$-$C_{10}$alkylene, $C_4$-$C_{10}$alkylene interrupted by 1, 2 or 3 oxygen atoms or by 1 or 2

groups where $R_{19}$ is as defined above for $R_{18}$ or is $C_1$-$C_6$acyl or ($C_1$-$C_6$alkoxy)carbonyl; or $R_{14}$ is further cyclohexylene, cyclohexylenedimethylene, methylenedicyclohexylene, isopropylidenedicyclohexylene, phenylene, phenylenedimethylene, methylenediphenylene or isopropylidenediphenylene, $R_{15}$ is $C_2$-$C_4$alkylene, $G_4$ is $>N-(R_{15}-G_3)_s-$, $>CH-O-$ or

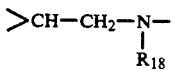

with $R_{18}$ as defined above, r and s which can be identical or different are zero or 1, $R_{16}$ is hydrogen or can also be methyl when r is 1 and $G_4$ is $>CH-O-$, and $R_{17}$ is hydrogen or methyl, $R_{12}$ is a direct bond, $C_1$-$C_{10}$alkylene, vinylene, cyclohexylene or phenylene, $R_{13}$ is $C_2$-$C_{10}$alkylene, $C_4$-$C_{10}$alkylene interrupted by 1, 2 or 3 oxygen atoms; cyclohexylene, cyclohexylenedimethylene or isopropylidenedicyclohexylene, and q is zero or an integer from 1 to 5, and, when n is 3, $R_5$ is aliphatic $C_4$-$C_{12}$triacyl, aromatic $C_9$-$C_{12}$triacyl or a group of the formula (VIII) in which $X_3$ is as defined above and $E_2$ is one of the groups of the formulae (IXa)-(IXc) in which $G_5$, $G_6$ and $G_7$ which can be identical or different are as defined above for $G_1$, $G_2$ and $G_3$; $R_{20}$, $R_{21}$ and $R_{22}$ which can be identical or different are $C_2$-$C_6$alkylene, t is zero or 1, $R_{23}$, $R_{24}$ and $R_{25}$ which can be identical or different are as defined above for $R_{18}$; $G_8$ is a direct bond or $-CH_2-$, u and v which can be identical or different are integers from 2 to 6 and $R_{26}$ is $C_3$-$C_{10}$alkanetriyl, and, when n is 4, $R_5$ is aliphatic $C_6$-$C_{12}$tetraacyl, aromatic $C_{10}$-$C_{12}$tetraacyl, tetrahydrofuran-2,3,4,5-tetracarbonyl or a group of the formula (X) in which $X_3$ is as defined above and $E_3$ is a group of the formulae (XIa)-(XIc) in which $G_9$ is as defined above for $G_1$, $G_2$ and $G_3$; $R_{27}$ and $R_{28}$ which can be identical or different are $C_2$-$C_6$alkylene, w is zero or 1 and $R_{29}$ is $C_4$-$C_8$alkanetetrayl.

Those compounds of the formula (I) are particularly preferred in which $R_2$ and $R_3$ which can be identical or different are $C_2$-$C_3$alkylene, $R_4$ is $-CO-$, $-COCO-$ or $-COCH_2CO-$, n is 1, 2, 3 or 4 and, when n is 1, $R_5$ is hydrogen, methyl, $C_4$-$C_{18}$alkyl, allyl, benzyl or one of the groups of the formulae (IIa)-(IIc) in which $X_1$ and $X_2$ which can be identical or different are a group $-OR_8$, $-SR_8$ or

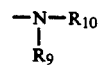

where $R_8$, $R_9$ and $R_{10}$ which can be identical or different are hydrogen, $C_1$-$C_{12}$alkyl, cyclohexyl which is unsubstituted or mono-, di- or tri-substituted by $C_1$-$C_4$alkyl; allyl, undecenyl, phenyl, benzyl, $C_2$-$C_3$alkyl substituted in the 2- or 3-position by OH, by $C_1$-$C_4$alkoxy, by dimethylamino, by diethylamino or by 4-morpholinyl; tetrahydrofurfuryl or a group of the formula (III), or the group

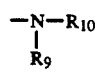

is 4-morpholinyl, or $X_1$ and $X_2$ are one of the groups of the formulae (IVa)-(IVd), $R_6$ is $C_2$-$C_{17}$alkyl, cyclohexyl which is unsubstituted or mono-, di- or tri-substituted by $C_1$-$C_4$alkyl; $C_2$-$C_{10}$alkenyl, phenyl, t-butylphenyl, 3,5-di-t-butyl-4-hydroxyphenyl, benzyl or 2-(3,5-di-t-butyl-4-hydroxyphenyl)ethyl, p is zero or 1 and $R_7$ is $C_2$-$C_{18}$alkyl, cyclohexyl which is unsubstituted or mono-, di- or tri-substituted by $C_1$-$C_4$alkyl; allyl, undecenyl, oleyl, benzyl or a group of the formula (III), and, when n is 2, $R_5$ is $C_2$-$C_8$alkylene, $C_4$-$C_8$alkylene interrupted by 1 or 2 oxygen atoms; 2-hydroxytrimethylene, phenylenedimethylene or one of the groups of the formulae (Va)-(Ve) in which $X_3$ is as defined above for $X_1$ and $X_2$ or is a group of the formula (VI), $E_1$ is one of the groups of the formulae (VIIa)-(VIIc) in which $G_1$, $G_2$ and $G_3$ which can be identical or different are $-O-$ or

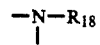

where $R_{18}$ is hydrogen, $C_1$-$C_{12}$alkyl, cyclohexyl which is unsubstituted or mono-, di- or tri-substituted by $C_1$-$C_4$alkyl; benzyl or a group of the formula (III), $R_{14}$ is $C_2$-$C_8$alkylene, $C_4$-$C_{10}$alkylene interrupted by 1, 2 or 3 oxygen atoms or by 1 or 2

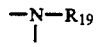

groups where $R_{19}$ is as defined above for $R_{18}$ or is $C_1$-$C_4$acyl or ($C_1$-$C_4$alkoxy)carbonyl; or $R_{14}$ is further cyclohexylenedimethylene, methylenedicyclohexylene, isopropylidenedicyclohexylene, phenylenedimethylene or isopropylidenediphenylene, $R_{15}$ is $C_2$-$C_3$alkylene, $G_4$ is $>N-(R_{15}-G_3)_s-$ or $>CH-O-$, r and s which can be identical or different are zero or 1, $R_{16}$ is hydrogen or can also be methyl when r is 1 and $G_4$ is $>CH-O-$, and $R_{17}$ is hydrogen or methyl, $R_{12}$ is a direct bond, $C_1$-$C_8$alkylene or phenylene, $R_{13}$ is $C_2$-$C_8$alkylene, $C_4$-$C_8$alkylene interrupted by 1 or 2 oxygen atoms; cyclohexylenedimethylene or isopropylidenedicyclohexylene and q is zero or an integer from 1 to 3, and, when n is 3, $R_5$ is aliphatic $C_4$-$C_8$triacyl, benzenetricarbonyl or a group of the formula (VIII) in which $X_3$ is as defined above and $E_2$ is one of the groups of the formulae (IXa)-(IXc) in which $G_5$, $G_6$ and $G_7$ which can be identical or different are as defined above for $G_1$, $G_2$ and $G_3$; $R_{20}$, $R_{21}$ and $R_{22}$ which can be identical or different are $C_2$–$C_4$alkylene, t is zero or 1, $R_{23}$, $R_{24}$ and $R_{25}$ which can be identical or different are as defined above for $R_{18}$; $G_8$ is a direct bond or —$CH_2$—, u and v which can be identical or different are integers from 3 to 6 and $R_{26}$ is $C_3$–$C_6$alkanetriyl, and, when n is 4, $R_5$ is aliphatic $C_6$–$C_8$tetraacyl, benzenetetracarbonyl, tetrahydrofuran-2,3,4,5-tetracarbonyl or a group of the formula (X) in which $X_3$ is as defined above and $E_3$ is a group of the formulae (XIa)–(XIc) in which $G_9$ is as defined above for $G_1$, $G_2$ and $G_3$; $R_{27}$ and $R_{28}$ which can be identical or different are $C_2$–$C_4$alkylene, w is zero or 1 and $R_{29}$ is $C_4$–$C_6$alkanetetrayl.

Those compounds of the formula (I) are of special interest in which $R_2$ and $R_3$ which can be identical or different are —$(CH_2)_2$— or —$(CH_2)_3$—, $R_4$ is —CO—, —COCO— or —COCH$_2$CO—, n is 1, 2, 3 or 4 and, when n is 1, $R_5$ is hydrogen, methyl, $C_8$–$C_{18}$alkyl, allyl or one of the groups of the formulae (IIa)–(IIc) in which $X_1$ and $X_2$ which can be identical or different are a group —$OR_8$ or

where $R_8$ is $C_1$–$C_8$alkyl or a group of the formula (III), $R_9$ and $R_{10}$ which can be identical or different are $C_1$–$C_8$alkyl, cyclohexyl, $C_2$–$C_3$alkyl substituted in the 2- or 3-position by methoxy, by ethoxy, by dimethylamino, by diethylamino or by 4-morpholinyl; or are tetrahydrofurfuryl or a group of the formula (III), or $R_9$ can also be hydrogen or the group

is 4-morpholinyl, $R_6$ is $C_3$–$C_{17}$alkyl, cyclohexyl, phenyl, 3,5-di-t-butyl-4-hydroxyphenyl or 2-(3,5-di-t-butyl-4-hydroxyphenyl)ethyl, p is zero, $R_7$ is $C_4$–$C_{18}$alkyl, cyclohexyl, t-butylcyclohexyl or a group of the formula (III), and, when n is 2, $R_5$ is one of the groups of the formulae (Va)–(Ve) in which $X_3$ is as defined above for $X_1$ and $X_2$ or is a group of the formula (VI), $E_1$ is one of the groups of the formulae (VIIa)–(VIIc) in which $G_1$ and $G_2$ which can be identical or different are —O— or

where $R_{18}$ is hydrogen, $C_1$–$C_8$alkyl, cyclohexyl or a group of the formula (III), $R_{14}$ is $C_2$–$C_6$alkylene, $C_6$–$C_{10}$alkylene interrupted by 2 or 3 oxygen atoms, cyclohexylenedimethylene or methylenedicyclohexylene, the group (VIIb) is one of the groups

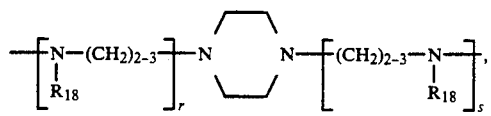

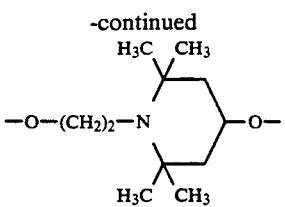

where r and s which can be identical or different are zero or 1, $R_{18}$ is as defined above and $R_{17}$ is hydrogen or methyl, $R_{12}$ is $C_2$–$C_8$alkylene or phenylene, $R_{13}$ is $C_4$–$C_8$alkylene or isopropylidenedicyclohexylene and q is zero or 1, and when n is 3, $R_5$ is a group of the formula (VIII) in which $X_3$ is as defined above and $E_2$ is a group of the formula (IXa) or (IXb) in which $G_5$ and $G_6$ which can be identical or different are as defined above for $G_1$ and $G_2$; $R_{20}$ and $R_{21}$ which can be identical or different are $C_2$–$C_3$alkylene, t is zero, $R_{23}$, $R_{24}$ and $R_{25}$ are as defined above for $R_{18}$; $G_8$ is a direct bond or —$CH_2$— and u and v which can be identical or different are integers from 3 to 5, and, when n is 4, $R_5$ is a group of the formula (X) in which $X_3$ is as defined above and $E_3$ is a group of the formula (XIa) in which $G_9$ is as defined above for $G_1$ and $G_2$; $R_{27}$ and $R_{28}$ which can be identical or different are $C_2$–$C_3$alkylene and w is zero or 1.

Those compounds of the formula (I) are of particular interest in which $R_1$ is hydrogen or methyl, $R_2$ and $R_3$ are —$(CH_2)_2$—, $R_4$ is —CO—, —COCO— or —COCH$_2$CO—, n is 1, 2, 3 or 4 and, when n is 1, $R_5$ is hydrogen, methyl, allyl or one of the groups of the formulae (IIa)–(IIc) in which $X_1$ and $X_2$ which can be identical or different are a group —$OR_8$ or

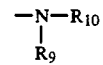

where $R_8$ is $C_1$–$C_4$alkyl, 2,2,6,6-tetramethyl-4-piperidyl or 1,2,2,6,6-pentamethyl-4-piperidyl, $R_9$ and $R_{10}$ which can be identical or different are $C_1$–$C_4$alkyl, cyclohexyl, tetrahydrofurfuryl, 2,2,6,6-tetramethyl-4-piperidyl or 1,2,2,6,6-pentamethyl-4-piperidyl or $R_9$ can also be hydrogen, or the group

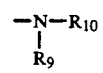

is 4-morpholinyl, $R_6$ is $C_4$–$C_{17}$alkyl or 2-(3,5-di-t-butyl-4-hydroxyphenyl)ethyl, p is zero and $R_7$ is $C_4$–$C_{18}$alkyl, and, when n is 2, $R_5$ is one of the groups of the formulae (Va)–(Vd) in which $X_3$ is as defined above for $X_1$ and $X_2$ or is a group of the formula (VI), $E_1$ is one of the groups

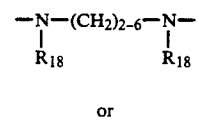

or

-continued

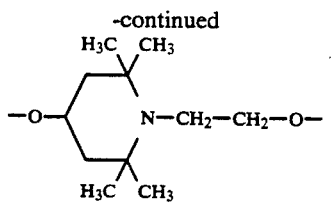

where $R_{18}$ is hydrogen, methyl, 2,2,6,6-tetramethyl-4-piperidyl or 1,2,2,6,6-pentamethyl-4-piperidyl, $R_{12}$ is $C_4$-$C_8$alkylene or phenylene and $R_{13}$ is $C_4$-$C_6$alkylene, and, when n is 3, $R_5$ is a group of the formula (VIII) in which $X_3$ is as defined above and $E_2$ is a group

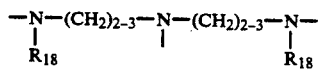

where $R_{18}$ is as defined above, and, when n is 4, $R_5$ is a group of the formula (X) in which $X_3$ is as defined above and $E_3$ is a group

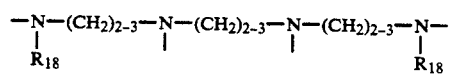

with $R_{18}$ as defined above.

Those compounds of the formula (I) are also of interest in which $R_1$ is hydrogen or methyl, $R_2$ and $R_3$ are —$(CH_2)_2$—, $R_4$ is —CO—, —COCO— or —COCH$_2$CO—, n is 1, 2 or 3 and, when n is 1, $R_5$ is hydrogen, allyl or one of the groups of the formulae (IIb) or (IIc) in which $R_6$ is $C_4$-$C_{17}$alkyl or 2-(3,5-di-t-butyl-4-hydroxyphenyl)ethyl, p is zero and $R_7$ is $C_4$-$C_{18}$alkyl, and, when n is 2, $R_5$ is one of the groups of the formulae (Vb) or (Vc) in which $X_3$ is a group of the formula (VI), $E_1$ is one of the groups

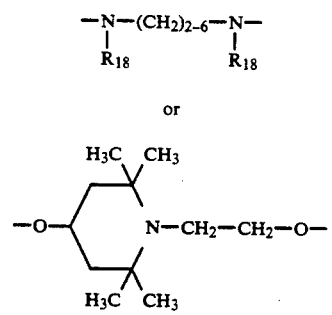

or

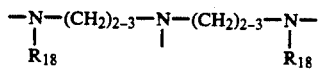

where $R_{18}$ is hydrogen, 2,2,6,6-tetramethyl-4-piperidyl or 1,2,2,6,6-pentamethyl-4-piperidyl, $R_{12}$ is phenylene and, when n is 3, $R_5$ is a group of the formula (VIII) in which $X_3$ is as defined above and $E_2$ is a group

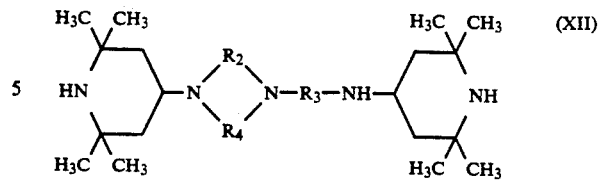

where $R_{18}$ is as defined above.

The compounds of the formula (I) can be prepared by processes known per se, for example by reacting a compound of the formula (XII)

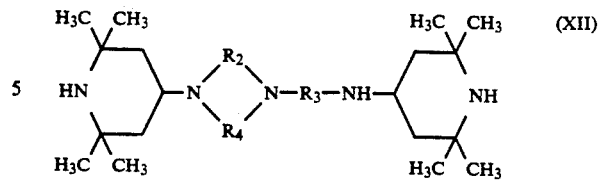

with suitable alkylating or acylating agents in the appropriate molar ratios.

In this way, the compounds of the formula (I) with $R_1$=H are obtained, from which the corresponding compounds with $R_1 \neq H$ can subsequently be obtained.

The reactions are conveniently carried out in an inert solvent, operating at temperatures from e.g. $-20°$ to $200°$ C., preferably from $-10°$ to $180°$ C.

The compounds of the formula (XII) can be prepared e.g. according to scheme 1 by reacting a compound of the formula (XIII) with a compound of the formula (XIV) in which A is —$NH_2$ or $C_1$-$C_4$alkoxy.

SCHEME 1

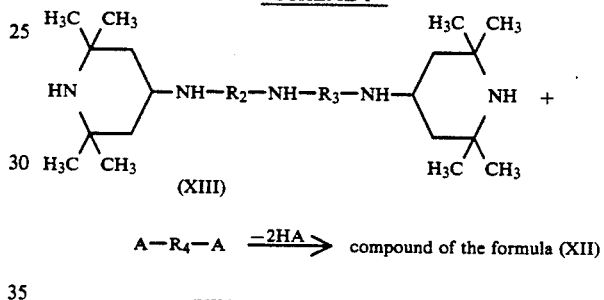

The reactions according to scheme 1 can be carried out in the presence or absence of an inert organic solvent at temperatures from e.g. $100°$ to $280°$ C., preferably from $150°$ to $250°$ C.

The compounds of the formula (XIII) can be prepared according to known processes for example by reductive alkylation of a triamine $H_2N$—$R_2$—NH—$R_3$—$NH_2$ with 2,2,6,6-tetramethyl-4-piperidone in the presence of a hydrogenation catalyst.

The compounds of the formula (XIV) are commercially available.

As mentioned at the outset, the compounds of the formula (I) are highly effective in improving the light stability, heat stability and oxidation stability of organic materials, in particular synthetic polymers and copolymers.

Examples of such organic materials which can be stabilised are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Copolymers of α-olefins with carbon monoxide, with regular or random alternation.

3b. Hydrocarbon resins (for example $C_5$–$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from copolymers of styrene and other polymers, such as, for example, from a polyacrylate, a diene polymer or an ethylene/propylene/diene terpolymer and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene; styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene; styrene and alkyl acrylates or methacrylates on polybutadiene; styrene and acrylonitrile on ethylene/propylene/diene terpolymers; styrene and acrylonitrile on polyacrylates or polymethacrylates; styrene and acrylonitrile on acrylate/butadiene copolymers, as well as mixtures thereof with the copolymers listed under 5), for instance the mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, such as for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers). 15. Polyamides and copolyamides which are derived from diamines and dicarboxylic acids and/or from aminocarboxylic acids or the corre-sponding lactams, such as polyamide 4, polyamide 6, polyamide 6/6, 6/10, 6/9, 6/12, 4/6, 12/12 polyamide 11, polyamide 12, aromatic polyamides obtained by condensation of m-xylene diamine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/[ch] or from hydroxycarboxylic acids or the corresponding lactones, such as polyethylene terephthalate, polybutylene terephthalate, poly-1,4-dimethylolcyclohexane terephthalate, poly-[2,2,-(4-hydroxyphenyl)-propane] terephthalate and polyhydroxybenzoates as well as block-copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilised, on the end use and on the presence of other additives.

In general, it is appropriate to use, for example, 0.01 to 5% by weight of the compounds of the formula (I), relative to the weight of the material to be stabilised, preferably between 0.05 and 1%.

In general, the compounds of the formula (I) can be incorporated in the polymeric materials before, during or after the polymerization or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilised with the products of the formula (I) can be used for the production of mouldings, films, tapes, monofilaments, fibres, surface coatings and the like.

If desired, other conventional additives for synthetic polymers, such as antioxidants, UV absorbers, nickel stabilisers, pigments, fillers, plasticisers, antistatic agents, flameproofing agents, lubricants, corrosion inhibitors and metal deactivators, can be added to the mixtures of the compounds of the formula (I) with the organic materials. The conventional additives are e.g. present in an amount of 0.01 to 10% by weight, relative to the weight of the organic material to be stabilized.

Particular examples of additives which can be used in admixture with the compounds of the formula (I) are:

1. Antioxidants 1.1. Alkylated monophenols, for example 2,6-di-tert-butyl-4-methyl-phenol, 2-tert-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexyl-phenol, 2,6-di-tert-butyl-4-methoxymethylphenol, 2,6-di-nonyl-4-methylphenol, 2,4-dimethyl-6-(1'-methyl-undec-1'-yl)-phenol, 2,4-dimethyl-6-(1'-methylheptadec-1'-yl)-phenol, 2,4-dimethyl-6-(1'-methyl-tridec-1'-yl)-phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl-stearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thio-bis-(3,6-di-sec-amylphenol), 4,4'-bis-(2,6-dimethyl-4-hydroxyphenyl)-disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis-(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butan, 2,2-bis-(3,5-di-tert.-butyl-4-hydroxyphenyl)-propan, 2,2-bis-(5-tert.-butyl-4- hydroxy-2-methylphenyl)-4-n-dodecylmercapto-butan, 1,1,5,5-tetra-(5-tert.-butyl-4-hydroxy-2-methylphenyl)-pentan.

1.6. O-, N- and S-benzyl compounds, for example 3,5,3',5'-tetra-tert.-butyl-4,4'-dihydroxydibenzylether, octadecyl-4-hydroxy-3,5-dimethylbenzyl-mercaptoacetate, tris-(3,5-di-tert.-butyl-4-hydroxybenzyl)-amine, bis-(4-tert.-butyl-3-hydroxy-2,6-dimethylbenzyl)dithioterephthalate, bis-(3,5-di-tert.-butyl-4-hydroxybenzyl)-sulfide, isooctyl-3,5-di-tert.-butyl-4-hydroxybenzyl-mercaptoacetate.

1.7. Hydroxybenzylated Malonates, for example di-octadecyl-2,2-bis-(3,5-di-tert.-butyl-2-hydroxybenzyl)-malonate, di-octadecyl-2-(3-tert.-butyl-4-hydroxy-5-methylbenzyl)-malonate, di-dodecylmercaptoethyl-2,2-bis-(3,5-di-tert.-butyl-4-hydroxybenzyl)-malonate, Di-[4-(1,1,3,3-tetramethylbutyl)-phenyl]-2,2-bis-(3,5-di-tert.-butyl-4-hydroxybenzyl)-malonate.

1.8. Hydroxybenzyl-Aromatics, for example 1,3,5-tris-(3,5-di-tert.-butyl-4-hydroxybenzyl)-2,4,6-trimethylbenzene, 1,4-bis-(3,5-di-tert.-butyl-4-hydroxybenzyl)-2,3,5,6-tetramethylbenzene, 2,4,6-tris-(3,5-di-tert.-butyl-4-hydroxybenzyl)-phenol.

1.9. Triazine Compounds, for example 2,4-bis-octylmercapto-6-(3,5-di-tert.-butyl-4-hydroxyanilino)-1,3,5-triazine, 2-octylmercapto-4,6-bis-(3,5-di-tert.-butyl-4-hydroxyanilino)-1,3,5-triazine, 2-octylmercapto-4,6-bis-(3,5-di-tert.-butyl-4-hydroxyphenoxy)-1,3,5-triazine, 2,4,6-tris-(3,5-di-tert.-butyl-4-hydroxyphenoxy)-1,2,3-triazine, 1,3,5-tris-(3,5-di-tert.-butyl-4-hydroxybenzyl)-isocyanurate, 1,3,5-tris-(4-tert.-butyl-3-hydroxy-2,6-dimethylbenzyl)-isocyanurate, 2,4,6-tris-(3,5-di-tert.-butyl-4-hydroxyphenylethyl)-1,3,5-triazine, 1,3,5-tris-(3,5-di-tert.butyl-4-hydroxyphenylpropionyl)-hexahydro-1,3,5-triazine, 1,3,5-tris-(3,5-dicyclohexyl-4-hydroxybenzyl)-isocyanurate.

1.10. Benzylphosphonates, for example dimethyl-2,5-di-tert.-butyl-4-hydroxybenzylphosphonate, diethyl-3,5-di-tert.-butyl-4-hydroxybenzylphosphonate, dioctadecyl-3,5-di-tert.-butyl-4-hydroxybenzylphosphonate, dioctadecyl-5-tert.-butyl-4-hydroxy-3-methylbenzylphosphonate, Ca-salt of the 3,5-di-tert.-butyl-4-hydroxybenzyl-phosphonic acid monoethylester.

1.11. Acylaminophenols, for example lauric acid 4-hydroxyanilide, stearic acid 4-hydroxyanilide, octyl N-(3,5-di-tert-butyl-4-hydroxyphenyl)-carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.14. Esters of β-(3,5-dicyclohexyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.15. Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylene-diamine, N,N'-bis(3,5-di-tert-butyl-4-hydroxyphenylpropionyl)-tri-methylene-diamine, N,N'-bis(3,5-di-tert-butyl-4-hydroxyphenylpropionyl)-hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl), mixture of 5-chloro-3'-tert.-butyl-5'-(2-octyloxycarbonylethyl)- and 5-chloro-3'-tert.-butyl-5'-[2-(2-ethylhexyloxy)-carbonylethyl]-, 5-chloro-3'-tert.-butyl-5'-(2-methoxycarbonylethyl)-, 3'-tert.-butyl-5'-(2-methoxycarbonylethyl)-, 3'-tert.-butyl-5'-(2-octyloxycarbonylethyl)-, 3'-tert.-butyl-5'-[2-(2-ethylhexyloxy)carbonylethyl]-, 3'-dodecyl-5'-methyl- and 3'-tert.-butyl-5'-(2-isooctyloxycarbonylethyl)-2'-hydroxyphenyl-2H-benztriazole(2), 2,2'-methylene-bis[4-(1,1,3,3-tetramethylbutyl)-6-benztriazole-2-yl-phenol]; product of ester interchange of 2-[3'-tert.-butyl-5'-(2-methoxycarbonylethyl)-2'-hydroxy-phenyl]-2H-benztriazole with polyethylene glycol 300; [R—CH$_2$CH$_2$—COO(CH$_2$)$_3$]$_2$ with R = 3'-tert.-butyl-4'-hydroxy-5'-2H-benzotriazole-2-yl-phenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert.butylphenyl salicylate, phenyl salicylate, octylphenyl salicylate, dibenzoylresorcinol, bis-(4-tert.butylbenzoyl)-resorcinol, benzoylresorcinol, 2,4-di-tert.butylphenyl 3,5-di-tert.butyl-4-hydroxybenzoate, hexadecyl 3,5-di-tert.butyl-4-hydroxybenzoate, octadecyl 3,5-di-tert.-butyl-4-hydroxybenzoate, 2 methyl-4,6-di-tert.-butylphenyl 3,5-di-tert.-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketoxime, nickel complexes of 1-phenyl-4-lauroyl-5-hydroxypyrazole, with or without additional ligands.

2.6. Sterically hindered amines, for example bis(2,2,6,6-tetramethyl-piperidyl) sebacate, bis-(2,2,6,6-tetramethyl-piperidyl) succinate, bis(1,2,2,6,6-pentamethylpiperidyl) sebacate, bis(1,2,2,6,6-pentamethylpiperidyl) n-butyl-3,5-di-tert-butyl-4-hydroxy-benzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis-(1,2,2,6,6-pentamethylpiperidyl)-2-n-butyl-2-(2-hydroxy-3,5-di-tert.-butylbenzyl) malonate, 3-n-octyl-7,7,9,9-tetramethyl-1,3,8-triazasprio[4.5]decan-2,4-dion, bis-(1-octyloxy-2,2,6,6-tetramethylpiperidyl) sebacate, bis-(1-octyloxy-2,2,6,6-tetramethylpiperidyl) succinate, product of condensation of N,N'-bis-(2,2,6,6-tetramethyl-4-piperidyl)-hexamethylene diamine and 4-morpholino-2,6-dichloro-1,3,5-triazine, product of condensation of -chloro-4,6-di-(4-n-butylamino-2,2,6,6-tetramethylpiperidyl)-1,3,5-triazine and 1,2-bis-(3-aminopropylamino)ethane, product of condensation of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dion, 3-dodecyl-1-(2,2,6,6-tetramethyl-4-piperidyl)pyrrolidin-2,5-dion, 3-dodecyl-1-(1,2,2,6,6-pentamethyl-4-piperidyl)-pyrrolidin-2,5-dion.

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylamino-propyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethyl)-1,3,5-triazine, 2-[2-hydroxy-4-(2-hydroxy-3-octyloxy-propyloxy)-phenyl]-4,6-bis(2,4-dimethyl)-1,3,5-triazine.

3. Metal deactivators, for example N,N'-diphenyloxalic acid diamide, N-salicylal-N'-salicyloylhydrazine, N,N'-bis(salicycloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide, Oxanilide, isophthalic acid dihydrazide, sebacic acid-bis-phenylhydrazide, N,N'-diacetal-adipinic acid dihydrazide, N,N'-bis-salicyloyl-oxalic acid dihydrazide, N,N'-bis-salicyloyl-thiopropionic acid dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl)-phosphite, diiso- decyl pentaerythritol diphosphite, bis(2,4-di-tert.-butylphenyl)pentaerythritol diphosphite, bis-(2,6-di-tert.-butyl-4-methylphenyl)-pentaerythritol diphosphite, bis-isodecyloxy-pentaerythritol diphosphite, bis-(2,4-di-tert.-butyl-6-methylphenyl)-pentaerythritol diphosphite, bis-(2,4,6-tri-tert.-butylphenyl)-pentaerythritol diphsophite, tristearyl sorbitol triphosphite, tetrakis(2,4-di-tert-butylphenyl)4,4'-biphenylene diphosphonite, 6-isooctyloxy-2,4,8,10-tetra-tert.-butyl-12H-dibenz[d,g]-1,3,2-dioxaphosphocin, 6-fluoro-2,4,8,10-tetra-tert.-butyl-12-methyl-dibenz[d,g]-1,3,2-dioxaphosphocin.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis(1-hydroxy-2,2,6,6-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecyl-mercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg behenate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The compounds of the formula (I) can also be used as stabilisers, especially as light stabilisers, for almost all materials known in the art of photographic reproduction and other reproduction techniques as e.g. described in Research Disclosure 1990, 31429 (pages 474 to 480).

Several examples of the preparation and use of the compounds of the formula (I) are reported for more detailed illustration of the present invention; these examples are given solely for illustrative purposes and do not imply any restriction. The compounds disclosed in the following Examples 1, 2, 13, 14, 16, 20 and 22 relate to a particularly preferred embodiment of the present invention.

EXAMPLE 1

Preparation of the compound of the formula

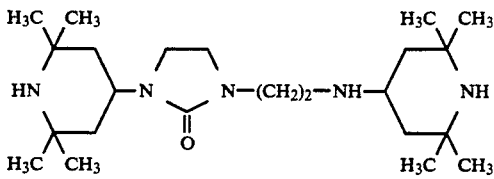

152.7 g (0.4 mol) of N,N'-bis(2,2,6,6-tetramethyl-4-piperidyl)diethylenetriamine and 26.4 g (0.44 mol) of urea are heated for 2 hours at 150° C. and for 2 hours at 230° C. under a gentle stream of nitrogen.

The product obtained is crystallised from octane. Melting point 93°-94° C.

Analysis for $C_{23}H_{45}N_5O$ Calculated: C=67.77%; H=11.13%; N=17.18%; Found: C=67.48%; H=11.05%; N=17.20%.

EXAMPLE 2

Preparation of the compound of the formula

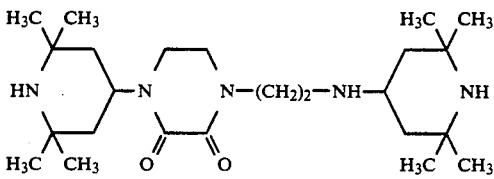

152.7 g (0.4 mol) of N,N'-bis(2,2,6,6-tetramethyl-4-piperidyl)diethylenetriamine, 47.2 g (0.4 mol) of dimethyl oxalate and 550 ml of trimethylbenzene are heated under reflux for 1 hour, with removal of the methanol formed in the reaction.

The reaction mixture is cooled to 5° C.; the precipitate formed is separated off by filtration, washed with acetone and dried. Melting point 237°-238° C.

Analysis for $C_{24}H_{45}N_5O_2$ Calculated: C=66.17%; H=10.41%; N=16.08%; Found: C=66.01%; H=10.38%; N=16.02%.

EXAMPLE 3

Preparation of the compound of the formula

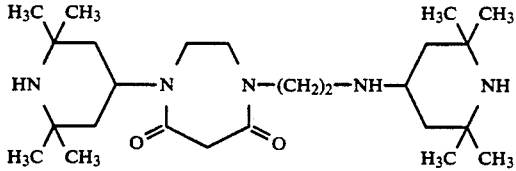

152.7 g (0.4 mol) of N,N'-bis(2,2,6,6-tetramethyl-4-piperidyl)diethylenetriamine and 58.1 g (0.44 mol) of dimethyl malonate are heated for 1 hour at 160°-190° C., with removal of the methanol formed in the reaction.

The product obtained is crystallised from methyl ethyl ketone. Melting point 205°-206° C.

Analysis for $C_{25}H_{47}N_5O_2$ Calculated: C=66.78%; H=10.53%; N=15.57%; Found: C=66.78%; H=10.52%; N=15.51%.

EXAMPLE 4

Preparation of the compound of the formula

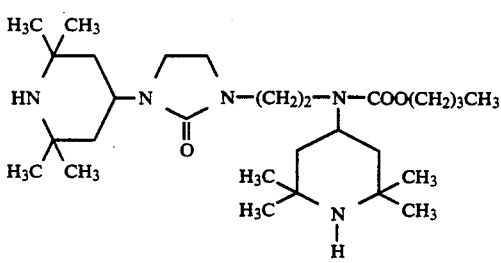

8.6 g (0.063 mol) of butyl chlorocarbonate are slowly added at a temperature not exceeding 0° C. to a solution, cooled to −10° C., of 24.5 g (0.06 mol) of the compound from Example 1 in 100 ml of 1,2-dichloroethane.

A solution of 2.6 g (0.065 mol) of sodium hydroxide in 25 ml of water is then added slowly, maintaining the temperature at 0° C. After the end of the addition, the reaction mixture is stirred for 1 hour at ambient temperature.

The aqueous layer is separated off and the organic phase is washed with water, dried over anhydrous $Na_2SO_4$ and evaporated in vacuo up to 70° C.

The product obtained is crystallised from hexane. Melting point 108°-109° C.

Analysis for $C_{28}H_{53}N_5O_3$ Calculated: C=66.23%; H=10.52%; N=13.79%; Found: C=66.30%; H=10.51%; N=13.78%.

EXAMPLE 5

The compound of the formula

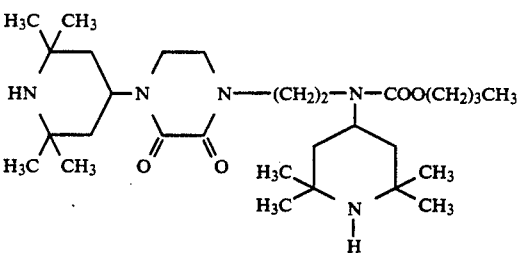

is prepared as described in Example 4, by reacting 7.2 g (0.053 mol) of butyl chlorocarbonate and 21.8 g (0.05 mol) of the compound from Example 2, in 150 ml of 1,2-dichloroethane.

The product obtained is crystallised from ethyl acetate. Melting point 178°-179° C.

Analysis for $C_{29}H_{53}N_5O_4$ Calculated: C=65.01%; H=9.97%; N=13.07%; Found: C=64.95%; H=9.90%; N=12.98%.

EXAMPLE 6

The compound of the formula

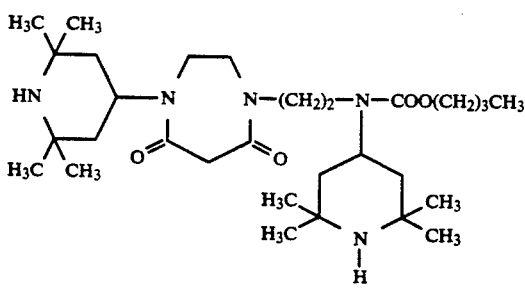

is prepared as described in Example 4 by reacting 7.2 g (0.053 mol) of butyl chlorocarbonate and 22.5 g (0.05 mol) of the compound from Example 3 in 150 ml of 1,2-dichloroethane.

The product is crystallised from hexane. Melting point 152°–153° C.

Analysis for $C_{30}H_{55}N_5O_4$ Calculated: C=65.54%; H=10.08%; N=12.74%; Found: C=65.46%; H=10.07%; N=12.70%.

EXAMPLE 7

The compound of the formula

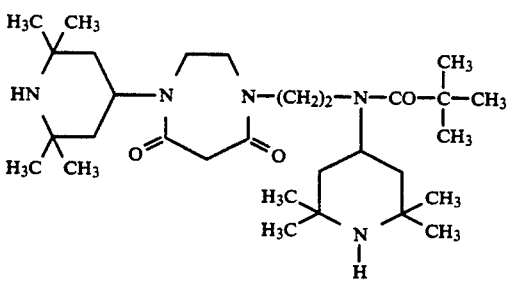

is prepared as described in Example 4 by reacting 6.6 g (0.055 mol) of pivaloyl chloride and 22.5 g (0.05 mol) of the compound from Example 3 in 250 ml of 1,2-dichloroethane.

The product obtained is crystallised from hexane. Melting point 193°–194° C.

Analysis for $C_{30}H_{55}N_5O_3$ Calculated: C=67.50%; H=10.38%; N=13.12%; Found: C=67.41%; H=10.32%; N=13.07%.

EXAMPLE 8

The compound of the formula

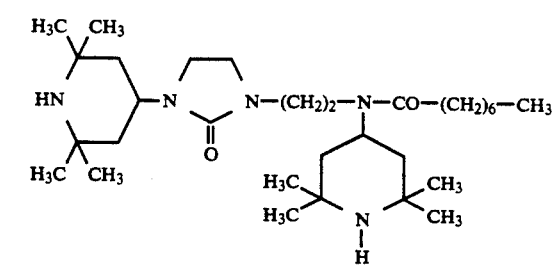

is prepared as described in Example 4 by reacting 10.2 g (0.063 mol) of octanoyl chloride and 24.5 g (0.06 mol) of the compound from Example 1 in 200 ml of 1,2-dichloroethane.

The product is crystallised from octane. Melting point 97°–98° C.

Analysis for $C_{31}H_{59}N_5O_2$ Calculated: C=69.75%; H=11.14%; N=13.12%; Found: C=69.78%; H=11.12%; N=13.11%.

EXAMPLE 9

Preparation of the compound of the formula

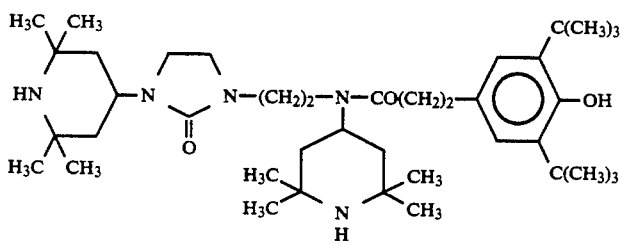

A solution of 14.8 g (0.05 mol) of 3-(3,5-di-t-butyl-4-hydroxyphenyl)propanoyl chloride in 50 ml of toluene is added slowly at ambient temperature to a solution of 20.4 g (0.05 mol) of the compound from Example 1 and 5.1 g (0.05 mol) of triethylamine in 100 ml of toluene. The mixture is stirred for one hour at ambient temperature and then heated for 2 hours at 60° C.

After cooling to ambient temperature, a solution of 2 g (0.05 mol) of sodium hydroxide in 25 ml of water is added and the mixture is stirred for 30 minutes.

The aqueous layer is separated off and the organic phase is washed with water, dried over anhydrous $Na_2SO_4$ and evaporated in vacuo up to 80° C.

The residue is crystallised from petroleum ether of boiling point 50°–70° C. Melting point 168°–169° C.

Analysis for $C_{40}H_{69}N_5O_3$ Calculated: C=71.92%; H=10.41%; N=10.48%; Found: C=72.01%; H=10.39%; N=10.43%.

EXAMPLE 10

Preparation of the compound of the formula

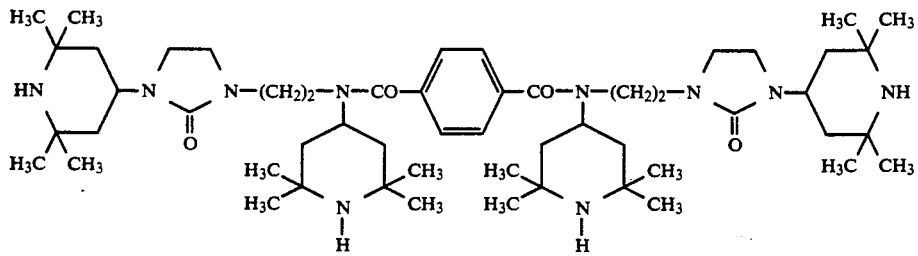

A solution of 5.1 g (0.025 mol) of terephthaloyl chloride in 80 ml of chloroform is added slowly to a solution of 20.4 g (0.05 mol) of the compound from Example 1 in 100 ml of chloroform, maintaining the temperature between 0° and 10° C.

The mixture is stirred for 12 hours at ambient temperature, and a solution of 2.1 g (0.0525 mol) of sodium hydroxide in 50 ml of water is then added slowly. After stirring for 1 hour at ambient temperature, the organic phase is separated off, washed with water, dried over anhydrous $Na_2SO_4$ and evaporated in vacuo up to 80° C.

The residue obtained is crystallised from acetone. Melting point 225°–226° C.

Analysis for $C_{54}H_{92}N_{10}O_4$ Calculated: C=68.61%; H=9.81%; N=14.82%; Found: C=68.29%; H=9.76%; N=14.72%.

EXAMPLE 11

Preparation of the compound of the formula

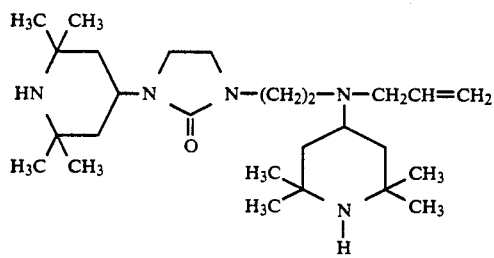

26.6 g (0.22 mol) of allyl bromide are added in 2 hours to a mixture, heated at 70° C., containing 81.5 g (0.2 mol) of the compound of Example 1, 400 ml of toluene, 8.8 g of sodium hydroxide and 40 ml of water.

At the end of the addition, the mixture is heated for 5 hours at 80° C. and then, the aqueous layer is separated off.

The solvent is evaporated in vacuo and the residue is crystallized from hexane.

The product so obtained has a melting point of 63°–65° C.

Analysis for $C_{26}H_{49}N_5O$ Calculated: C=69.75%; H=11.03%; N=15.64%; Found: C=69.40%; H=10.90%; N=15.57%.

EXAMPLE 12

The compound of the formula

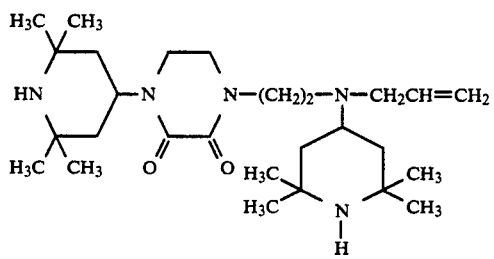

is prepared as described in Example 11, using the compound of Example 2.

The product obtained has a melting point of 162°–164° C.

Analysis for $C_{27}H_{49}N_5O_2$ Calculated: C=68.17%; H=10.38%; N=14.72%; Found: C=67.69%; H=10.35%; N=14.67%.

EXAMPLE 13

Preparation of the compound of the formula

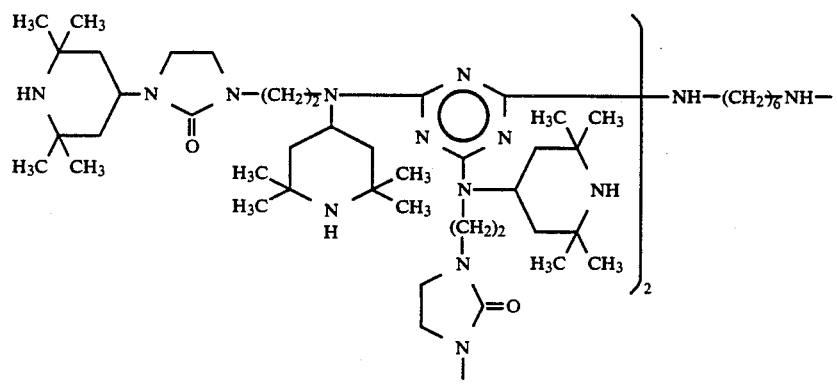

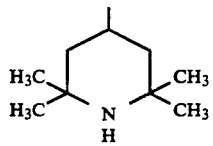

81.5 g (0.2 mol) of the compound from Example 1 are added slowly to a solution, cooled to 10° C., of 18.5 g (0.1 mol) of cyanuric chloride in 220 ml of xylene, maintaining the temperature between 10° and 20° C.

After the end of the addition, the mixture is stirred for 1 hour at ambient temperature, 8 g (0.2 mol) of sodium hydroxide dissolved in 30 ml of water are added, the mixture is heated for 2 hours at 70° C., and the aqueous layer is then separated off.

5.8 g (0.05 mol) of 1,6-hexanediamine and 8 g (0.2 mol) of ground sodium hydroxide are added, and the mixture is heated under reflux for 16 hours, the water of reaction being separated off azeotropically.

200 ml of xylene are added, and the mixture is filtered hot. After cooling to ambient temperature, the precipitate formed is separated off by filtration and dried in vacuo.

Melting point 151°–153° C.

Analysis for $C_{104}H_{190}N_{28}O_4$ Calculated: C=65.85%; H=10.10%; N=20.68%; Found: C=66.05%; H=10.02%; N=20.57%.

EXAMPLES 14–17

Following the procedure described in Example 13 and using the respective reagents in the appropriate molar ratios, the following compounds of the formula

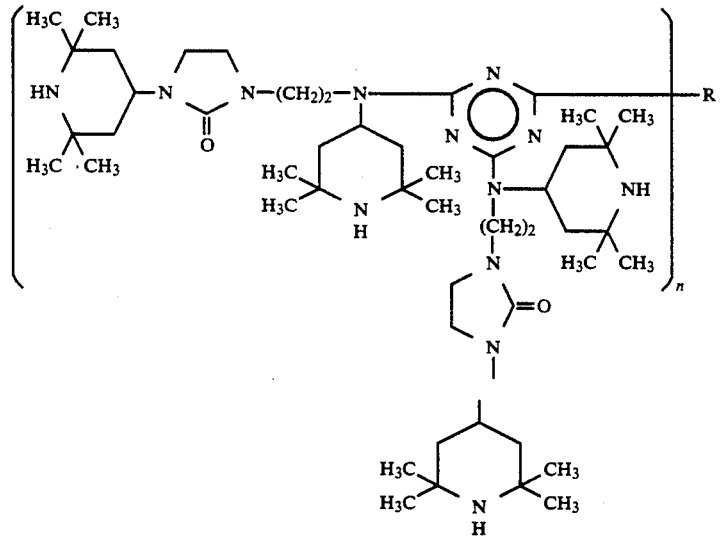

are prepared.

| Example | n | R | Melting point (°C.) |
|---|---|---|---|
| 14 | 2 | —N(piperidinyl)—(CH$_2$)$_6$—N(piperidinyl)— | 156–157 |
| 15 | 2 | —O—(piperidinyl)—N—CH$_2$CH$_2$O— | 154–156 |
| 16 | 3 | —NH—(CH$_2$)$_3$—N—(CH$_2$)$_3$—NH— | 156–157 |

-continued

| Example | n | R | Melting point (°C.) |
|---|---|---|---|
| 17 | 3 | (structure shown) | 171-173 |

EXAMPLE 18

Preparation of the compound of the formula

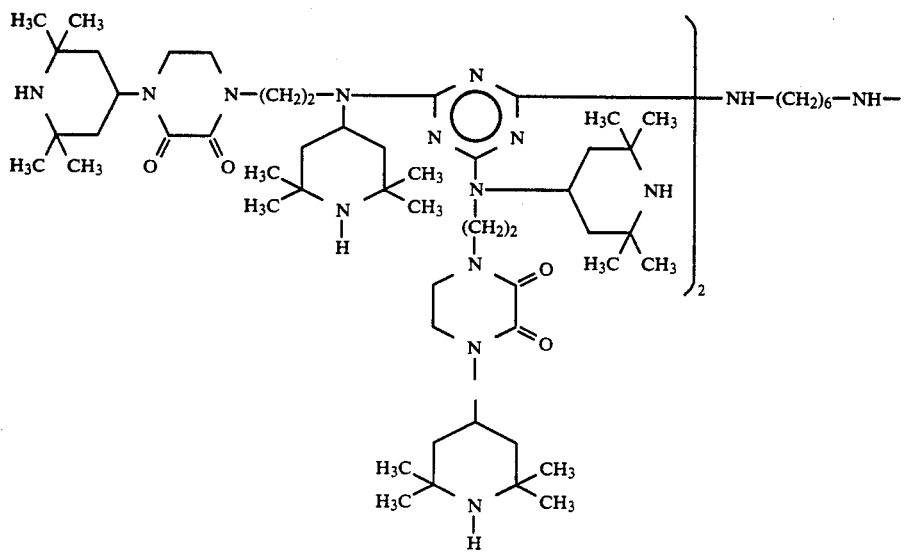

87.12 g (0.2 mol) of the compound of Example 2 are slowly added to a solution, cooled at 10° C., of 18.5 g (0.1 mol) of cyanuric chloride in 220 ml of xylene, maintaining the temperature between 10° and 20° C. After the end of the addition, the mixture is stirred for 1 hour at ambient temperature. 8 g (0.12 mol) of sodium hydroxide dissolved in 30 ml of water are added, the mixture is heated for 2 hours at 70° C. and then, the aqueous layer is separated off. The solvent is evaporated in vacuo and the residue is dissolved in 800 ml of 2-methoxyethylether. Subsequently, 5.8 g (0.05 mol) of 1,6-hexanediamine and 5.5 g of potassium carbonate are added and the mixture is heated at reflux for 8 hours. After cooling to ambient temperature, the precipitate formed is separated off by filtration, dissolved in 400 ml of dichloromethane and washed with water. Then, the organic solvent is evaporated and the residue is dried in vacuo.

The product obtained has a melting point of 257°-259° C.

Analysis for $C_{108}H_{190}N_{28}O_8$ Calculated: C=64.57%; H=9.53%; N=19.52%; Found: C=64.50%; H=9.51%; N=19.36%.

EXAMPLES 19-20

Following the procedure described in Example 18 and using the respective reagents in the appropriate molar ratios, the following compounds of the formula

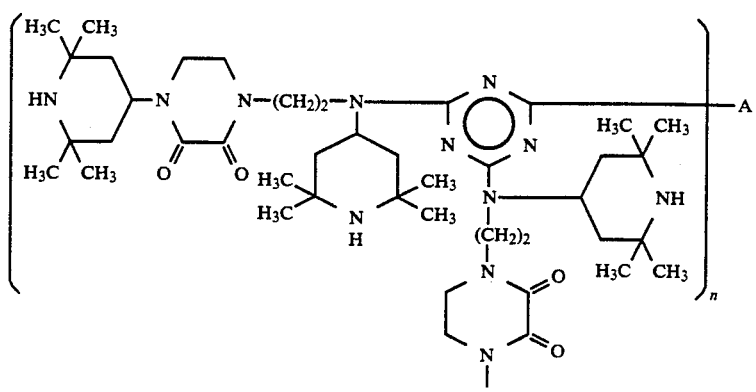

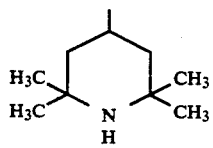

are prepared.

| Example | m | A | Melting point (°C.) |
|---------|---|---|---------------------|
| 19 | 2 | —N—(CH$_2$)$_6$—N— with two 2,2,6,6-tetramethylpiperidin-4-yl groups (NH) | 302–304 |
| 20 | 3 | —NH—(CH$_2$)$_3$—N—(CH$_2$)$_3$—NH— | 198–201 |

EXAMPLE 21

Preparation of the compound of the formula

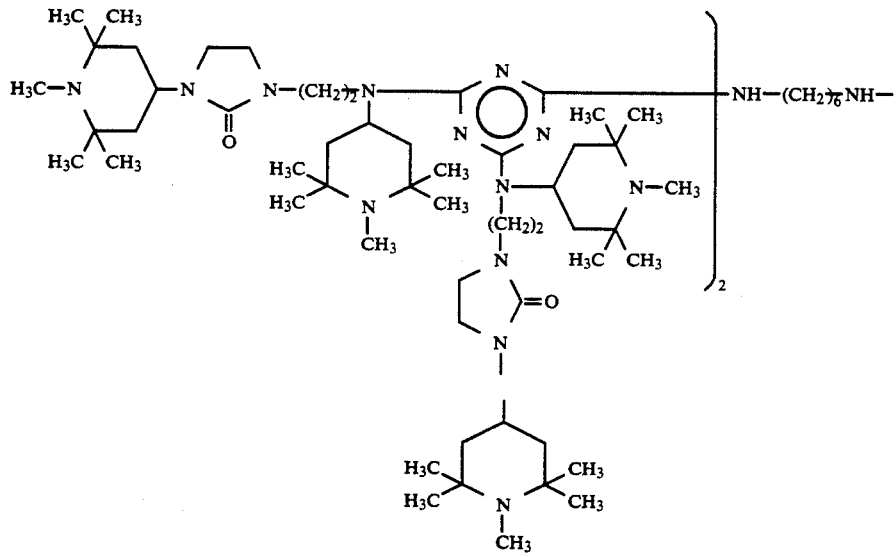

A solution containing 3 g (0.1 mol) of formaldehyde and 4.6 g (0.1 mol) of formic acid in 10 ml of water is added in 3 hours to a solution, heated to 110° C., of 19 g (0.01 mol) of the compound from Example 13 in 100 ml of xylene, with simultaneous removal of the water added and of the water of reaction.

The mixture is then cooled to 70° C., a solution of 6 g of sodium hydroxide in 50 ml of water is added, and the mixture is stirred for 30 minutes.

After separating off the aqueous phase, the organic layer is washed with water, dried over anhydrous Na$_2$SO$_4$ and evaporated under reduced pressure. The product obtained is washed with hexane and dried. Melting point 241°–243° C.

Analysis for C$_{112}$H$_{206}$N$_{28}$O$_4$ Calculated: C=66.96%; H=10.33%; N=19.52%; Found: C=66.57%; H=10.29%; N=19.41%.

EXAMPLE 22

The compound of the formula

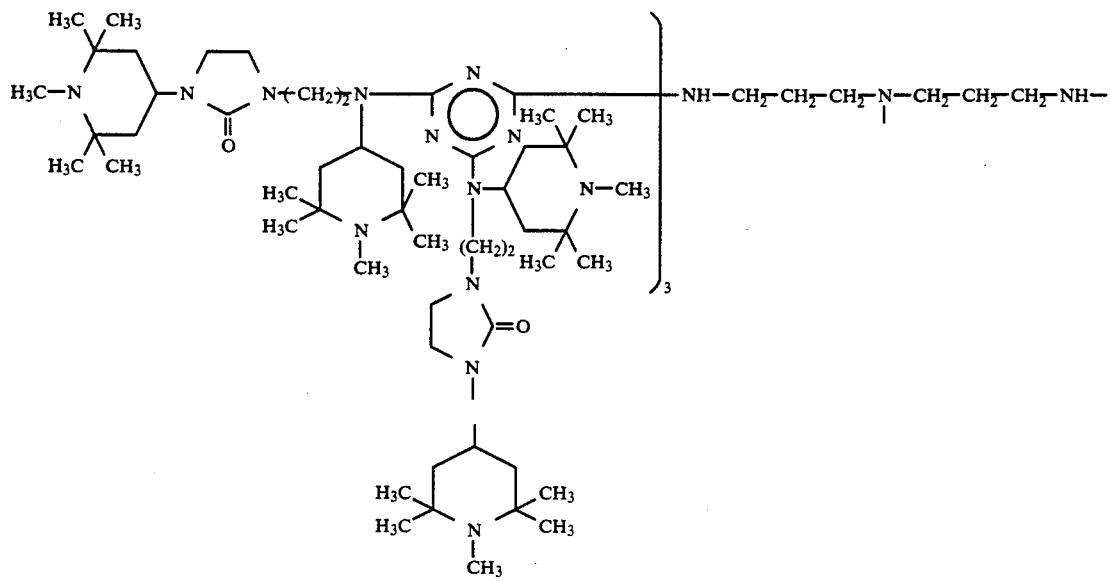

is prepared as described in Example 21, using the compound from Example 16.

The product obtained is crystallised from hexane. Melting point 181°–183° C.

Analysis for $C_{165}H_{302}N_{42}O_6$ Calculated: C=66.72%; H=10.25%; N=19.80%; Found: C=67.01%; H=10.21%; N=19.81%.

EXAMPLE 23

The compound of the formula is prepared as described in Example 21, using the compound of Example 14.

The melting point of the product obtained is 221°–223° C.

Analysis for $C_{132}H_{244}N_{30}O_4$ Calculated: C=68.47%; H=10.62%; N=18.15%; Found: C=67.90%; N=10.59%; N=18.06%.

EXAMPLE 24

The compound of the formula

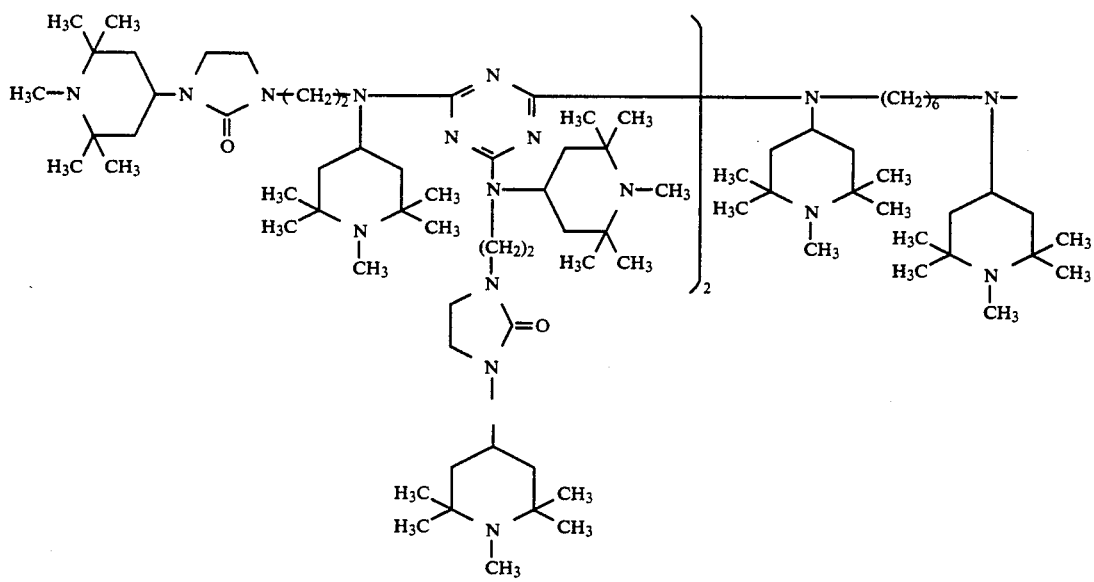

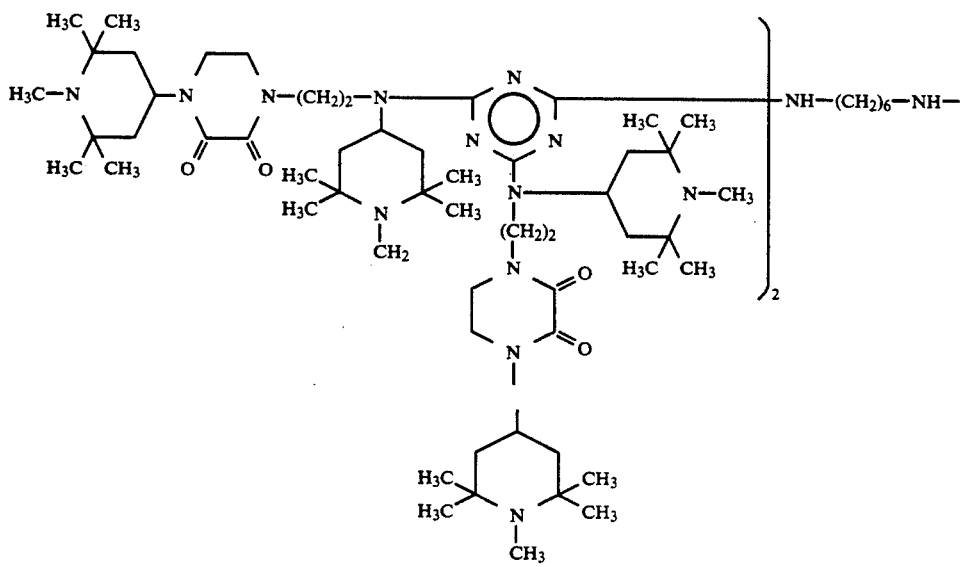

is prepared as described in Example 21, using the compound of Example 18.

The melting point of the product obtained is 285°–287° C.

Analysis for $C_{116}H_{206}N_{28}O_8$ Calculated: C=65.69%; H=9.79%; N=18.49%; Found: C=65.03%; H=9.73%; N=18.39%.

EXAMPLE 25 light-stabilising action in polypropylene fibres 2.5 g of each of the products indicated in Table 1, 1 g of tris(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°–230° C. to give polymer granules which are then converted into fibres, using a pilot-type apparatus (®Leonard-Sumirago (VA) Italy) operating under the following conditions:

| | |
|---|---|
| Extruder temperature: | 200–230° C. |
| Head temperature: | 255–260° C. |
| Stretch ratio: | 1:3.5 |
| Count: | 11 dtex per filament |

The fibres thus prepared are exposed, mounted on a white card, in a model 65WR Weather-O-Meter (ASTM D 2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated.

Fibres prepared under the same conditions as indicated above, but without addition of stabilisers of the invention, are exposed for comparison.

The results obtained are shown in Table 1.

TABLE 1

| Stabiliser | $T_{50}$ hours |
|---|---|
| Without stabiliser | 130 |
| Compound from Example 13 | 1400 |
| Compound from Example 14 | 1500 |
| Compound from Example 15 | 1240 |

EXAMPLE 26 light-stabilising action in polypropylene tapes 1 g of each of the products indicated in Table 2, 0.5 g of tris(2,4-di-t-butylphenyl) phosphite, 0.5 g of pentaerythritol tetrakis-[3-(3,5-di-tert-butyl-4-hydroxyphenyl)propionate] and 1 g of calcium stearate are mixed in a slow mixer with 1000 g of polypropylene powder of melt index=12 g/10 minutes (measured at 230° C. and 2.16 kg).

The mixtures are extruded at 200°–220° C. to give polymer granules which are then converted into stretched tapes of 50 μm thickness and 2.5 mm width, using a pilot-type apparatus (®Leonard-Sumirago (VA) Italy) operating under the following conditions:

| | |
|---|---|
| Extruder temperature: | 210–230° C. |
| Head temperature: | 240–260° C. |
| Stretch ratio: | 1:6 |

The tapes thus prepared are exposed, mounted on a white card, in a model 65WR Weather-O-Meter (ASTM D 2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated.

Tapes prepared under the same conditions as indicated above, but without addition of stabilisers of the invention, are exposed for comparison.

The results obtained are shown in Table 2.

TABLE 2

| Stabiliser | T₅₀ hours |
| --- | --- |
| Without stabiliser | 500 |
| Compound from Example 13 | 2850 |
| Compound from Example 14 | 2820 |
| Compound from Example 16 | 2740 |

What is claimed is:

1. A compound of the formula (I)

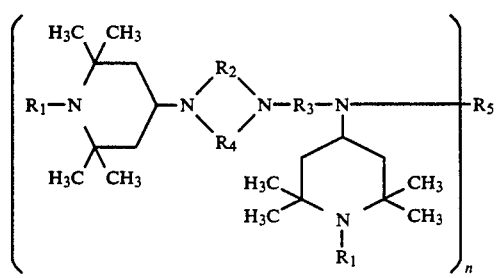
(I)

in which $R_1$ is hydrogen, $C_1$-$C_8$alkyl, O, OH, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di- or tri-substituted on the phenyl by $C_1$-$C_4$alkyl; or $C_1$-$C_8$acyl, $R_2$ and $R_3$ which can be identical or different are $C_2$-$C_3$alkylene, $R_4$ is —CO—, —COCO— or —COCH$_2$CO—, n is 1, 2, 3 or 4, and, when n is 1, $R_5$ is hydrogen, $C_1$-$C_{18}$alkyl, $C_3$-$C_6$alkenyl, $C_7$-$C_9$phenylalkyl which is unsubstituted or mono-, di- or tri-substituted on the phenyl by $C_1$-$C_4$alkyl; or $R_5$ is one of the groups of the formulae (IIa)-(IIc)

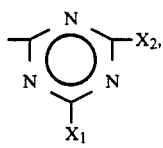
(IIa)

—COR$_6$, (IIb)

—(CO)$_p$COR$_7$ (IIc)

in which $X_1$ and $X_2$ which can be identical or different are a group —OR$_8$, —SR$_8$ or

where $R_8$, $R_9$ and $R_{10}$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl; $C_3$-$C_{18}$alkenyl, phenyl which is unsubstituted or mono-, di- or tri-substituted by $C_1$-$C_4$alkyl or $C_1$-$C_4$alkoxy; $C_7$-$C_9$phenylalkyl which is unsubstituted or mono-, di- or tri-substituted on the phenyl by $C_1$-$C_4$alkyl; $C_2$-$C_4$alkyl substituted in the 2, 3- or 4-position by OH, by $C_1$-$C_8$alkoxy, by di($C_1$-$C_4$alkyl)amino or by a nitrogen-containing to 7-membered heterocyclic group with the free valency on the nitrogen atom; tetrahydrofurfuryl or a group of the formula (III)

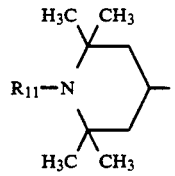
(III)

where $R_{11}$ is as defined for $R_1$, or

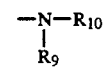

is a 5- to 7-membered heterocyclic group, or $X_1$ and $X_2$ are one of the groups of the formulae (IVa)-(IVd)

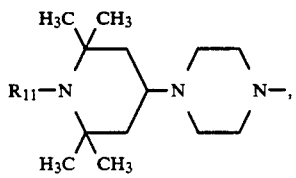
(IVa)

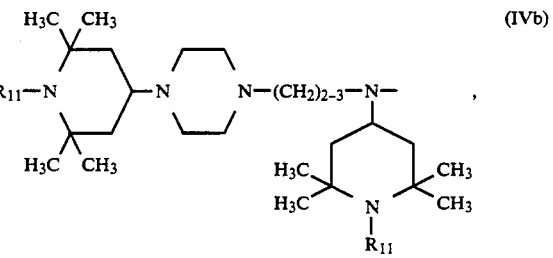
(IVb)

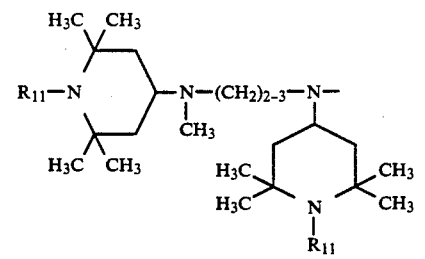
(IVc)

(IVd)

with $R_{11}$ as defined above, $R_6$ is hydrogen, $C_1$-$C_{18}$alkyl, $C_5$-$C_{12}$cycloalkyl which is unsubstituted or mono-, di- or tri-substituted by $C_1$-$C_4$alkyl; $C_2$-$C_{18}$alkenyl, phenyl which is unsubstituted or mono-, di- or tri-substituted by $C_1$-$C_4$alkyl or $C_1$-$C_4$alkoxy and/or by an OH group; $C_7$-$C_9$phenylalkyl which is unsubstituted or mono-, di- or tri-substituted on the phenyl by $C_1$-$C_4$alkyl and/or an OH group; p is zero or 1, and $R_7$ is $C_1$-$C_{18}$alkyl, $C_5$-$C_{12}$cycloalkyl which is unsubstituted or mono-, di- or tri-substituted by $C_1$-$C_4$alkyl; $C_3$-$C_{18}$alkenyl, $C_7$-$C_9$phenylalkyl which is unsubstituted or mono-, di- or tri-substituted on the phenyl by $C_1$-$C_4$alkyl; or a group of the formula (III), and, when n is 2, $R_5$ is $C_2$-$C_{12}$alkylene, $C_4$-$C_{12}$alkylene interrupted by 1, 2 or 3 oxygen atoms; 2-hydroxytrimethylene, phenylenedimethylene or one of the groups of the formulae (Va)-(Ve)

$$\begin{array}{c} N \\ \diagup \diagdown \\ -N \diagdown \diagup N- \\ X_3 \end{array} \quad \text{(Va)}$$

$$\left\{ \begin{array}{c} N \\ \diagup \diagdown \\ -N \diagdown \diagup N- \\ X_3 \end{array} \right\}_2 - E_1, \quad \text{(Vb)}$$

$$-CO-R_{12}-CO-, \quad \text{(Vc)}$$

$$-COO-R_{13}-OOC-, \quad \text{(Vd)}$$

$$-(CH_2)_q CO- \quad \text{(Ve)}$$

in which $X_3$ is as defined above for $X_1$ and $X_2$ or is a group of the formula (VI)

$$\begin{array}{c} H_3C \ CH_3 \\ R_1-N \quad \diagup N-R_3-N- \\ \diagdown \diagup R_4 \\ H_3C \ CH_3 \end{array} \begin{array}{c} H_3C \quad CH_3 \\ H_3C \quad CH_3 \\ N \\ R_1 \end{array} \quad \text{(VI)}$$

where $R_1$, $R_2$, $R_3$ and $R_4$ are as defined above, $E_1$ is one of the groups of the formulae (VIIa)-(VIIc)

$$-G_1-R_{14}-G_2-, \quad \text{(VIIa)}$$

$$\begin{array}{c} R_{16} \ R_{16} \\ \diagup \diagdown \\ +G_3-R_{15}\!\!\!+_rN \quad G_4-, \\ \diagdown \diagup \\ R_{16} \ R_{16} \end{array} \quad \text{(VIIb)}$$

$$\begin{array}{c} \diagup \diagdown \\ -N \quad N- \\ R_{17} \diagdown \diagup R_{17} \end{array} \quad \text{(VIIc)}$$

in which $G_1$, $G_2$ and $G_3$ which can be identical or different are —O— or $$-N-R_{18}$$

where $R_{18}$ is hydrogen, $C_1$-$C_{18}$alkyl, $C_5$-$C_{12}$cycloalkyl which is unsubstituted or mono-, di- or tri-substituted by $C_1$-$C_4$alkyl; $C_7$-$C_9$phenylalkyl which is unsubstituted or mono-, di- or tri-substituted on the phenyl by $C_1$-$C_4$alkyl; or a group of the formula (III), $R_{14}$ is $C_2$-$C_{12}$alkylene, $C_4$-$C_{12}$alkylene interrupted by 1, 2 or 3 oxygen atoms or by 1 or 2

$$-N-R_{19}$$

groups where $R_{19}$ is as defined above for $R_{18}$ or is $C_1$-$C_8$acyl or ($C_1$-$C_8$alkoxy)carbonyl; or $R_{14}$ is further $C_5$-$C_7$cycloalkylene unsubstituted or substituted by $C_1$-$C_4$alkyl; $C_5$-$C_7$cycloalkylenedi($C_1$-$C_4$alkylene), $C_1$-$C_4$alkylenedi($C_5$-$C_7$cycloalkylene), $C_2$-$C_4$alkylidenedi($C_5$-$C_7$cycloalkylene), phenylene unsubstituted or substituted by $C_1$-$C_4$alkyl; phenylenedi($C_1$-$C_4$alkylene), $C_1$-$C_4$alkylenediphenylene or $C_2$-$C_4$alkylidenediphenylene, $R_{15}$ is $C_2$-$C_6$alkylene, $G_4$ is one of the groups $>N-(R_{15}-G_3)_s$, $>CH-O-$ or $$>CH-CH_2-N-\\ \quad\quad\quad | \\ \quad\quad\quad R_{18}$$

with $R_{18}$ as defined above, r and s which can be identical or different are zero or 1, $R_{16}$ is hydrogen or can also be methyl when r is 1 and $G_4$ is $>CH-O-$, and $R_{17}$ is hydrogen or methyl, $R_{12}$ is a direct bond, $C_1$-$C_{12}$alkylene, $C_2$-$C_4$alkenylene, cyclohexylene, cyclohexenylene or phenylene, $R_{13}$ is $C_2$-$C_{12}$alkylene, $C_4$-$C_{12}$alkylene interrupted by 1, 2 or 3 oxygen atoms, $C_5$-$C_7$cycloalkylene unsubstituted or substituted by $C_1$-$C_4$alkyl; $C_5$-$C_7$cycloalkylenedi($C_1$-$C_4$alkylene) or $C_2$-$C_4$alkylidenedi($C_5$-$C_7$cycloalkylene) and q is zero or an integer from 1 to 10, and when n is 3, $R_5$ is aliphatic $C_4$-$C_{18}$triacyl, aromatic $C_9$-$C_{18}$triacyl or a group of the formula (VIII)

$$\left\{ \begin{array}{c} N \\ \diagup \diagdown \\ -N \diagdown \diagup N- \\ X_3 \end{array} \right\}_3 - E_2 \quad \text{(VIII)}$$

in which $X_3$ is as defined above and $E_2$ is one of the groups of the formula (IXa)-(IXc)

$$-G_5-R_{20}-N-R_{21}-G_6-, \quad \text{(IXa)}$$
$$\quad\quad\quad\quad\quad | \\ \quad\quad\quad\quad\quad \left( \begin{array}{c} R_{22} \\ | \\ G_7 \end{array} \right)_t$$

$$\begin{array}{c} -N-(CH_2)_u-CH-(CH_2)_v-N- \\ | \quad\quad\quad | \quad\quad\quad | \\ R_{23} \quad\quad G_8 \quad\quad R_{24} \\ \quad\quad | \\ \quad\quad N-R_{25} \end{array} \quad \text{(IXb)}$$

$$R_{26}+O\!\!+_{\overline{5}} \quad \text{(IXc)}$$

in which $G_5$, $G_6$ and $G_7$ which can be identical or different are as defined above for $G_1$, $G_2$ and $G_3$; $R_{20}$, $R_{21}$ and $R_{22}$ which can be identical or different are $C_2$-$C_6$alkylene, t is zero or 1, $R_{23}$, $R_{24}$ and $R_{25}$ which can be identical or different are as defined above for $R_{18}$; $G_8$ is a direct bond or —CH$_2$—, u and v which can be identical or different are integers from 2 to 6 and $R_{26}$ is $C_3$-$C_{12}$alkanetriyl, and, when n is 4, $R_5$ is aliphatic $C_6$-$C_{18}$tetraacyl, aromatic $C_{10}$-$C_{18}$tetraacyl, tetrahydrofuran-2,3,4,5-tetracarbonyl or a group of the formula (X)

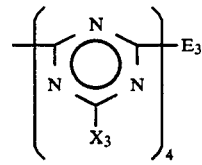
(X)

in which $X_3$ is as defined above and $E_3$ is one of the groups of the formulae (XIa)-(XIc)

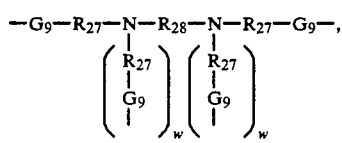
(XIa)

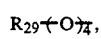
(XIb)

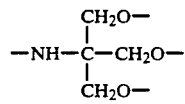
(XIc)

in which $G_9$ is as defined above for $G_1$, $G_2$ and $G_3$; $R_{27}$ and $R_{28}$ which can be identical or different are $C_2$-$C_6$alkylene, w is zero or 1 and $R_{29}$ is $C_4$-$C_{12}$alkanetetrayl.

2. A compound of the formula (I) according to claim 1, in which $R_1$ and $R_{11}$ which can be identical or different are hydrogen, $C_1$-$C_4$alkyl, OH, $C_6$-$C_{12}$alkoxy, $C_5$-$C_8$cycloalkoxy, allyl, benzyl or acetyl.

3. A compound of the formula (I) according to claim 1, in which $R_2$ and $R_3$ which can be identical or different are $C_2$-$C_3$alkylene, $R_4$ is —CO—, —COCO— or —COCH$_2$CO—, n is 1, 2, 3 or 4 and, when n is 1, $R_5$ is hydrogen, $C_1$-$C_{18}$alkyl, $C_3$-$C_4$alkenyl, benzyl which is unsubstituted or mono-, di- or tri-substituted on the phenyl by $C_1$-$C_4$alkyl; or $R_5$ is one of the groups of the formulae (IIa)-(IIc) in which $X_1$ and $X_2$ which can be identical or different are a group —OR$_8$, —SR$_8$ or

where $R_8$, $R_9$ and $R_{10}$ which can be identical or different are hydrogen, $C_1$-$C_{18}$alkyl, $C_5$-$C_8$cycloalkyl which is unsubstituted or mono-, di- or tri-substituted by $C_1$-$C_4$alkyl; $C_3$-$C_{18}$alkenyl, phenyl which is unsubstituted or mono-, di- or tri-substituted by $C_1$-$C_4$alkyl or $C_1$-$C_4$alkoxy; benzyl which is unsubstituted or mono-, di- or tri-substituted on the phenyl by $C_1$-$C_4$alkyl; $C_2$-$C_3$alkyl substituted in the 2- or 3- position by OH, by $C_1$-$C_4$alkoxy, by di($C_1$-$C_4$alkyl)amino or by a group

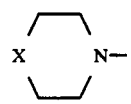

where X is a direct bond, —O—, —CH$_2$— or —CH$_2$CH$_2$—; tetrahydrofurfuryl or a group of the formula (III), or the group

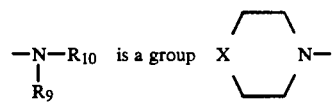

as defined above, or $X_1$ and $X_2$ are one of the groups of the formulae (IVa)-(IVd), $R_6$ is hydrogen, $C_1$-$C_{17}$alkyl, $C_5$-$C_8$cycloalkyl which is unsubstituted or mono-, di- or tri-substituted by $C_1$-$C_4$alkyl; $C_2$-$C_{17}$alkenyl, phenyl which is unsubstituted or mono-, di- or tri-substituted by $C_1$-$C_4$alkyl or $C_1$-$C_4$alkoxy and/or an OH group; benzyl or phenylethyl which both are unsubstituted or mono-, di- or tri-substituted on the phenyl by $C_1$-$C_4$alkyl and/or an OH group; p is zero or 1, $R_7$ is $C_1$-$C_{18}$alkyl, $C_5$-$C_8$cycloalkyl which is mono-, di- or tri-substituted by $C_1$-$C_4$alkyl; $C_3$-$C_{18}$alkenyl, benzyl which is unsubstituted or mono-, di- or trisubstituted on the phenyl by $C_1$-$C_4$alkyl; or a group of the formula (III), and, when n is 2, $R_5$ is $C_2$-$C_{10}$alkylene, $C_4$-$C_{10}$alkylene interrupted by 1, 2 or 3 oxygen atoms; 2-hydroxytrimethylene, phenylenedimethylene or one of the groups of the formulae (Va)-(Ve) in which $X_3$ is as defined above for $X_1$ and $X_2$ or is a group of the formula (VI), $E_1$ is one of the groups of the formulae (VIIa)-(VIIc) in which $G_1$, $G_2$ and $G_3$ which can be identical or different are —O— or

where $R_{18}$ is hydrogen, $C_1$-$C_{18}$alkyl, $C_5$-$C_8$cycloalkyl which is unsubstituted or mono-, di- or tri-substituted by $C_1$-$C_4$alkyl; benzyl which is unsubstituted or mono-, di- or tri-substituted on the phenyl by $C_1$-$C_4$alkyl; or a group of the formula (III), $R_{14}$ is $C_2$-$C_{10}$alkylene, $C_4$-$C_{10}$alkylene interrupted by 1, 2 or 3 oxygen atoms or by 1 or 2

groups where $R_{19}$ is as defined above for $R_{18}$ or is $C_1$-$C_6$acyl or ($C_1$-$C_6$alkoxy)carbonyl; or $R_{14}$ is further cyclohexylene, cyclohexylenedimethylene, methylenedicyclohexylene, isopropylidenedicyclohexylene, phenylene, phenylenedimethylene, methylenediphenylene or isopropylidenediphenylene, $R_{15}$ is $C_2$-$C_4$alkylene, $G_4$ is >N—($R_{15}$—$G_3$)$_s$—, >CH—O— or

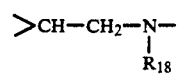

with $R_{18}$ as defined above, r and s which can be identical or different are zero or 1, $R_{16}$ is hydrogen or can also be methyl when r is 1 and $G_4$ is >CH—O—, and $R_{17}$ is hydrogen or methyl, $R_{12}$ is a direct bond, $C_1$-$C_{10}$alkylene, vinylene, cyclohexylene or phenylene, $R_{13}$ is $C_2$-$C_{10}$alkylene, $C_4$-$C_{10}$alkylene interrupted by 1, 2 or 3 oxygen atoms; cyclohexylene, cyclohexylenedimethylene or isopropylidenedicyclohexylene, and q is zero or an integer from 1 to 5, and, when n is 3, $R_5$ is aliphatic $C_4$-$C_{12}$triacyl, aromatic $C_9$-$C_{12}$triacyl or a group of the formula (VIII) in which $X_3$ is as defined above and $E_2$ is one of the groups of the formulae (IXa)-(IXc) in which $G_5$, $G_6$ and $G_7$ which can be identical or different are as defined above for $G_1$, $G_2$ and $G_3$; $R_{20}$, $R_{21}$ and $R_{22}$ which can be identical or different are $C_2$-$C_6$alkylene, t is zero or 1, $R_{23}$, $R_{24}$ and $R_{25}$ which can be identical or different are as defined above for $R_{18}$; $G_8$ is a direct bond or —$CH_2$—, u and v which can be identical or different are integers from 2 to 6 and $R_{26}$ is $C_3$-$C_{10}$alkanetriyl, and, when n is 4, $R_5$ is aliphatic $C_6$-$C_{12}$tetraacyl, aromatic $C_{10}$-$C_{12}$tetraacyl, tetrahydrofuran-2,3,4,5-tetracarbonyl or a group of the formula (X) in which $X_3$ is as defined above and $E_3$ is a group of the formulae (XIa)-(XIc) in which $G_9$ is as defined above for $G_1$, $G_2$ and $G_3$; $R_{27}$ and $R_{28}$ which can be identical or different are $C_2$-$C_6$alkylene, w is zero or 1 and $R_{29}$ is $C_4$-$C_8$alkanetetrayl.

4. A compound of the formula (I) according to claim 1, in which $R_2$ and $R_3$ which can be identical or different are $C_2$-$C_3$alkylene, $R_4$ is —CO—, —COCO— or —COCH$_2$CO—, n is 1, 2, 3 or 4 and, when n is 1, $R_5$ is hydrogen, methyl, $C_4$-$C_{18}$alkyl, allyl, benzyl or one of the groups of the formulae (IIa)-(IIc) in which $X_1$ and $X_2$ which can be identical or different are a group —$OR_8$, —$SR_8$ or

where $R_8$, $R_9$ and $R_{10}$ which can be identical or different are hydrogen, $C_1$-$C_{12}$allyl, cyclohexyl which is unsubstituted or mono-, di- or tri-substituted by $C_1$-$C_4$alkyl; allyl, undecenyl, phenyl, benzyl, $C_2$-$C_3$alkyl substituted in the 2- or 3-position by OH, by $C_1$-$C_4$alkoxy, by dimethylamino, by diethylamino or by 4-morpholinyl; tetrahydrofurfuryl or a group of the formula (III), or the group

is 4-morpholinyl, or $X_1$ and $X_2$ are one of the groups of the formulae (IVa)-(IVd), $R_6$ is $C_2$-$C_{17}$alkyl, cyclohexyl which is unsubstituted or mono-, di- or tri-substituted by $C_1$-$C_4$alkyl; $C_2$-$C_{10}$alkenyl, phenyl, t-butylphenyl, 3,5-di-t-butyl-4-hydroxyphenyl, benzyl or 2-(3,5-di-t-butyl-4-hydroxyphenyl)ethyl, p is zero or 1 and $R_7$ is $C_2$-$C_{18}$alkyl, cyclohexyl which is unsubstituted or mono-, di- or tri-substituted by $C_1$-$C_4$alkyl; allyl, undecenyl, oleyl, benzyl or a group of the formula (III), and, when n is 2, $R_5$ is $C_2$-$C_8$alkylene, $C_4$-$C_8$alkylene interrupted by 1 or 2 oxygen atoms; 2-hydroxytrimethylene, phenylenedimethylene or one of the groups of the formulae (Va)-(Ve) in which $X_3$ is as defined above for $X_1$ and $X_2$ or is a group of the formula (VI), $E_1$ is one of the groups of the formulae (VIIa)-(VIIc) in which $G_1$, $G_2$ and $G_3$ which can be identical or different are —O— or

where $R_{18}$ is hydrogen, $C_1$-$C_{12}$alkyl, cyclohexyl which is unsubstituted or mono-, di- or tri-substituted by $C_1$-$C_4$alkyl; benzyl or a group of the formula (III), $R_{14}$ is $C_2$-$C_8$alkylene, $C_4$-$C_{10}$alkylene interrupted by 1, 2 or 3 oxygen atoms or by 1 or 2

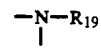

groups where $R_{19}$ is as defined above for $R_{18}$ or is $C_1$-$C_4$acyl or ($C_1$-$C_4$alkoxy)carbonyl; or $R_{14}$ is further cyclohexylenedimethylene, methylenedicyclohexylene, isopropylidenedicyclohexylene, phenylenedimethylene or isopropylidenediphenylene, $R_{15}$ is $C_2$-$C_3$alkylene, $G_4$ is >N—($R_{15}$—$G_3$)$_s$— or >CH—O—, r and s which can be identical or different are zero or 1, $R_{16}$ is hydrogen or can also be methyl when r is 1 and $G_4$ is >CH—O—, and $R_{17}$ is hydrogen or methyl, $R_{12}$ is a direct bond, $C_1$-$C_8$alkylene or phenylene, $R_{13}$ is $C_2$-$C_8$alkylene, $C_4$-$C_8$alkylene interrupted by 1 or 2 oxygen atoms; cyclohexylenedimethylene or isopropylidenedicyclohexylene and q is zero or an integer from 1 to 3, and, when n is 3, $R_5$ is aliphatic $C_4$-$C_8$triacyl, benzenetricarbonyl or a group of the formula (VIII) in which $X_3$ is as defined above and $E_2$ is one of the groups of the formulae (IXa)-(IXc) in which $G_5$, $G_6$ and $G_7$ which can be identical or different are as defined above for $G_1$, $G_2$ and $G_3$; $R_{20}$, $R_{21}$ and $R_{22}$ which can be identical or different are $C_2$-$C_4$alkylene, t is zero or 1, $R_{23}$, $R_{24}$ and $R_{25}$ which can be identical or different are as defined above for $R_{18}$; $G_8$ is a direct bond or —$CH_2$—, u and v which can be identical or different are integers from 3 to 6 and $R_{26}$ is $C_3$-$C_6$alkanetriyl, and, when n is 4, $R_5$ is aliphatic $C_6$-$C_8$tetraacyl, benzenetetracarbonyl, tetrahydrofuran-2,3,4,5-tetracarbonyl or a group of the formula (X) in which $X_3$ is as defined above and $E_3$ is a group of the formulae (XIa)-(XIc) in which $G_9$ is as defined above for $G_1$, $G_2$ and $G_3$; $R_{27}$ and $R_{28}$ which can be identical or different are $C_2$-$C_4$alkylene, w is zero or 1 and $R_{29}$ is $C_4$-$C_6$alkanetetrayl.

5. A compound of the formula (I) according to claim 1, in which $R_2$ and $R_3$ which can be identical or different are —($CH_2$)$_2$— or —($CH_2$)$_3$—, $R_4$ is —CO—, —COCO— or —COCH$_2$CO—, n is 1, 2, 3 or 4 and, when n is 1, $R_5$ is hydrogen, methyl, $C_8$-$C_{18}$alkyl, allyl or one of the groups of the formulae (IIa)-(IIc) in which $X_1$ and $X_2$ which can be identical or different are a group —$OR_8$ or

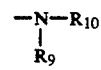

where $R_8$ is $C_1$-$C_8$alkyl or a group of the formula (III), $R_9$ and $R_{10}$ which can be identical or different are $C_1$-$C_8$alkyl, cyclohexyl, $C_2$-$C_3$alkyl substituted in the 2- or 3-position by methoxy, by ethoxy, by dimethylamino, by diethylamino or by 4-morpholinyl; or are tetrahydrofurfuryl or a group of the formula (III), $R_9$ can also be hydrogen or the group

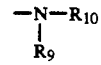

is 4-morpholinyl, $R_6$ is $C_3$-$C_{17}$alkyl, cyclohexyl, phenyl, 3,5-di-t-butyl-4-hydroxyphenyl or 2-(3,5-di-t-butyl-4- hydroxyphenyl)ethyl, p is zero, $R_7$ is $C_4$-$C_{18}$alkyl, cyclohexyl, t-butylcyclohexyl or a group of the formula (III), and, when n is 2, $R_5$ is one of the groups of the formulae (Va)-(Ve) in which $X_3$ is as defined above for $X_1$ and $X_2$ or is a group of the formula (VI), $E_1$ is one of the groups of the formulae (VIIa)-(VIIc) in which $G_1$ and $G_2$ which can be identical or different are —O— or

where $R_{18}$ is hydrogen, $C_1$-$C_8$alkyl, cyclohexyl or a group of the formula (III), $R_{14}$ is $C_2$-$C_6$alkylene, $C_6$-$C_{10}$alkylene interrupted by 2 or 3 oxygen atoms, cyclohexylenedimethylene or methylenedicyclohexylene, the group (VIIb) is one of the groups

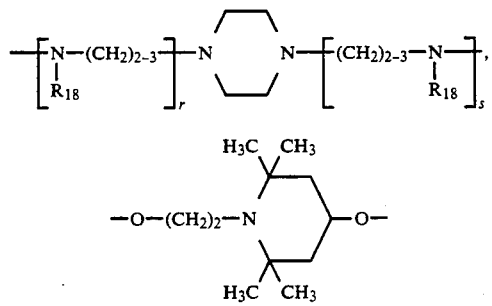

where r and s which can be identical or different are zero or 1, $R_{18}$ is as defined above and $R_{17}$ is hydrogen or methyl, $R_{12}$ is $C_2$-$C_8$alkylene or phenylene, $R_{13}$ is $C_4$-$C_8$alkylene or isopropylidenedicyclohexylene and q is zero or 1, and when n is 3, $R_5$ is a group of the formula (VIII) in which $X_3$ is as defined above and $E_2$ is a group of the formula (IXa) or (IXb) in which $G_5$ and $G_6$ which can be identical or different are as defined above for $G_1$ and $G_2$; $R_{20}$ and $R_{21}$ which can be identical or different are $C_2$-$C_3$alkylene, t is zero, $R_{23}$, $R_{24}$ and $R_{25}$ are as defined above for $R_{18}$; $G_8$ is a direct bond or —$CH_2$— and u and v which can be identical or different are integers from 3 to 5, and, when n is 4, $R_5$ is a group of the formula (X) in which $X_3$ is as defined above and $E_3$ is a group of the formula (XIa) in which $G_9$ is as defined above for $G_1$ and $G_2$; $R_{27}$ and $R_{28}$ which can be identical or different are $C_2$-$C_3$alkylene and w is zero or 1.

6. A compound of the formula (I) according to claim 1, in which $R_1$ is hydrogen or methyl, $R_2$ and $R_3$ are —$(CH_2)_2$—, $R_4$ is —CO—, —COCO— or —COCH$_2$CO—, n is 1, 2, 3 or 4 and, when n is 1, $R_5$ is hydrogen, methyl, allyl or one of the groups of the formulae (IIa)-(IIc) in which $X_1$ and $X_2$ which can be identical or different are a group —$OR_8$ or

where $R_8$ is $C_1$-$C_4$alkyl, 2,2,6,6-tetramethyl-4-piperidyl or 1,2,2,6,6-pentamethyl-4-piperidyl, $R_9$ and $R_{10}$ which can be identical or different are $C_1$-$C_4$alkyl, cyclohexyl, tetrahydrofurfuryl, 2,2,6,6-tetramethyl-4-piperidyl or 1,2,2,6,6-pentamethyl-4-piperidyl or $R_9$ can also be hydrogen, or the group

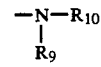

is 4-morpholinyl, $R_6$ is $C_4$-$C_{17}$alkyl or 2-(3,5-di-t-butyl-4-hydroxyphenyl)ethyl, p is zero and $R_7$ is $C_4$-$C_{18}$alkyl, and, when n is 2, $R_5$ is one of the groups of the formulae (Va)-(Vd) in which $X_3$ is as defined above for $X_1$ and $X_2$ or is a group of the formula (VI), $E_1$ is one of the groups

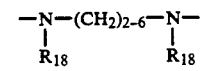

or

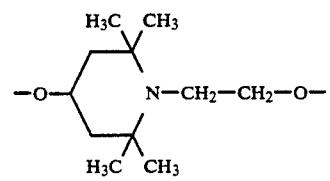

where $R_{18}$ is hydrogen, methyl, 2,2,6,6-tetramethyl-4-piperidyl or 1,2,2,6,6-pentamethyl-4-piperidyl, $R_{12}$ is $C_4$-$C_8$alkylene or phenylene and $R_{13}$ is $C_4$-$C_6$alkylene, and, when n is 3, $R_5$ is a group of the formula (VIII) in which $X_3$ is as defined above and $E_2$ is a group

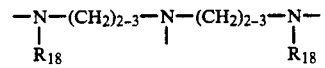

where $R_{18}$ is as defined above, and, when n is 4, $R_5$ is a group of the formula (X) in which $X_3$ is as defined above and $E_3$ is a group

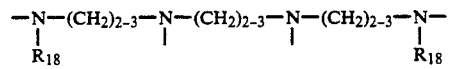

with $R_{18}$ as defined above.

7. A compound of the formula (I) according to claim 1, in which $R_1$ is hydrogen or methyl, $R_2$ and $R_3$ are —$(CH_2)_2$—, $R_4$ is —CO—, —COCO— or —COCH$_2$CO—, n is 1, 2 or 3 and, when n is 1, $R_5$ is hydrogen, allyl or one of the groups of the formulae (IIb) or (IIc) in which $R_6$ is $C_4$-$C_{17}$alkyl or 2-(3,5-di-t-butyl-4-hydroxyphenyl)ethyl, p is zero and $R_7$ is $C_4$-$C_{18}$alkyl, and, when n is 2, $R_5$ is one of the groups of the formulae (Vb) or (Vc) in which $X_3$ is a group of the formula (VI), $E_1$ is one of the groups

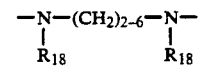

or

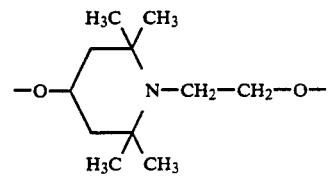

where $R_{18}$ is hydrogen, 2,2,6,6-tetramethyl-4-piperidyl or 1,2,2,6,6-pentamethyl-4-piperidyl, $R_{12}$ is phenylene and, when n is 3, $R_5$ is a group of the formula (VIII) in which $X_3$ is as defined above and $E_2$ is a group
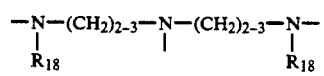
where $R_{18}$ is as defined above
8. A compound of the formula
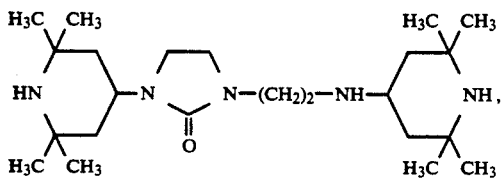
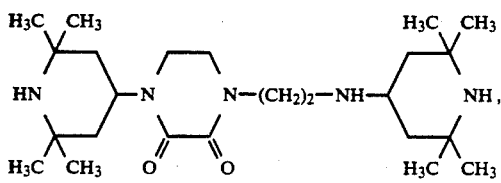
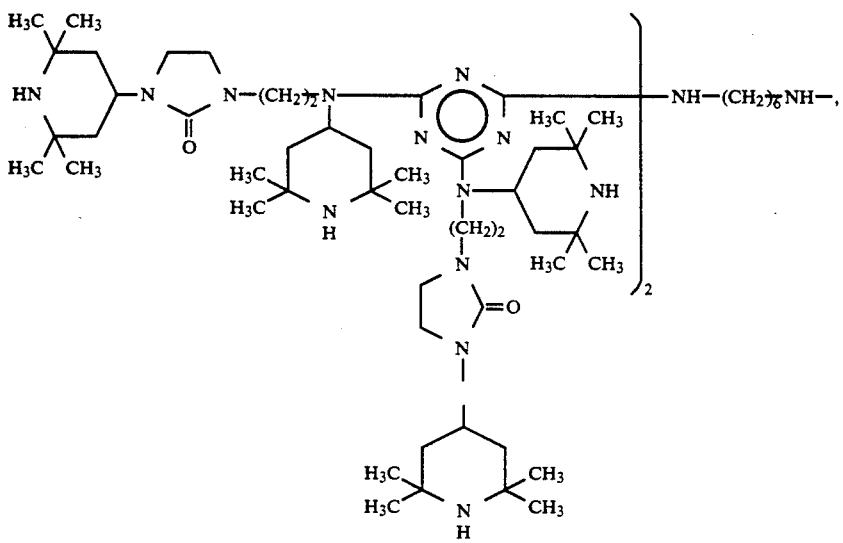
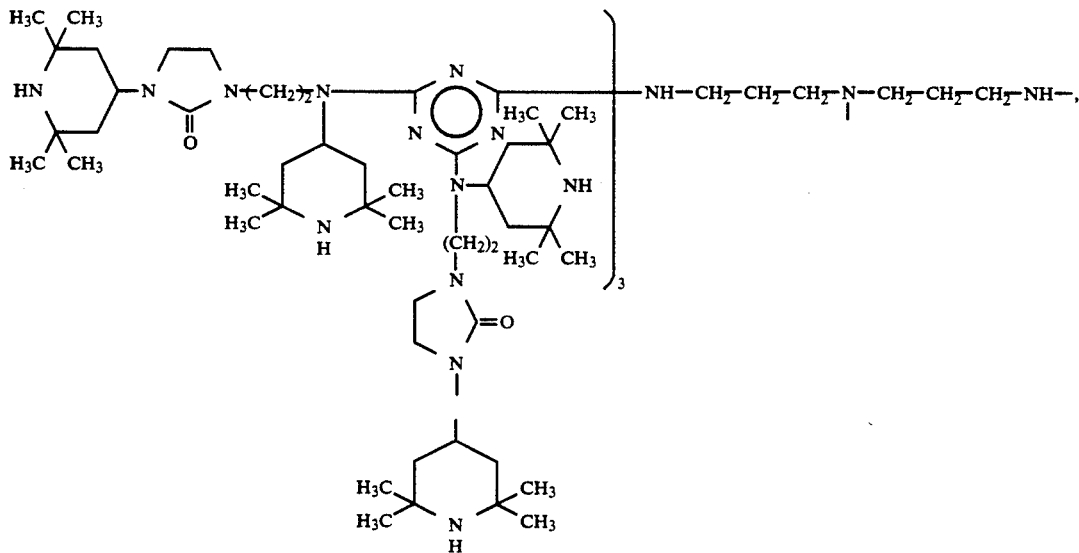

-continued
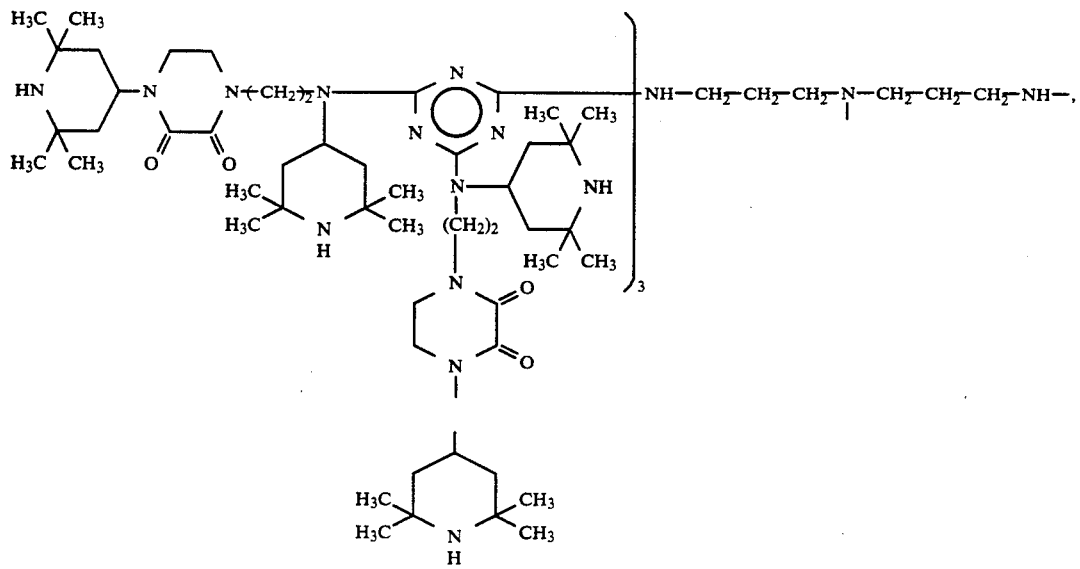
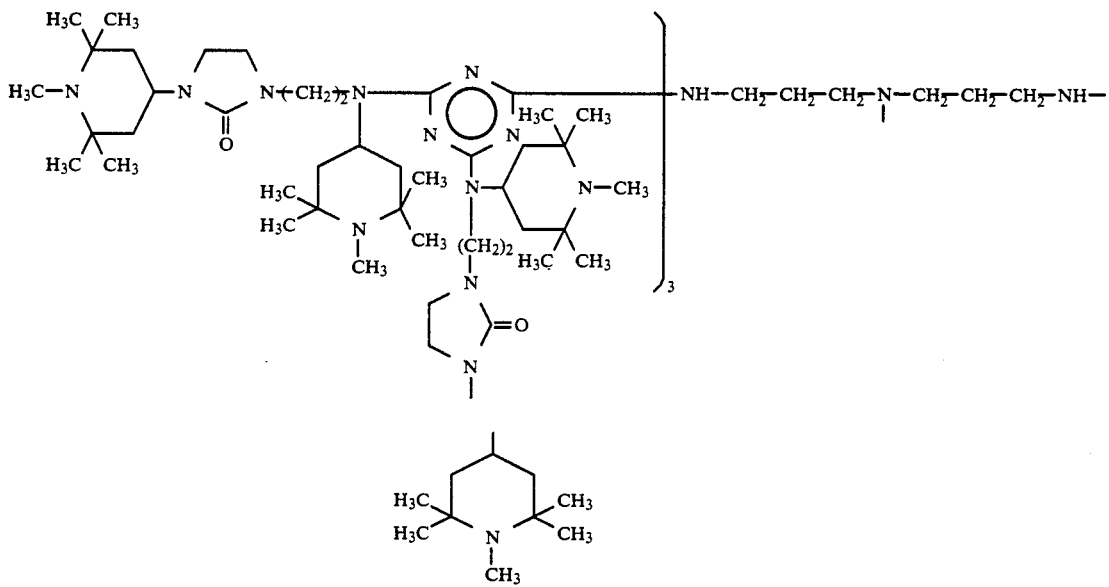
or
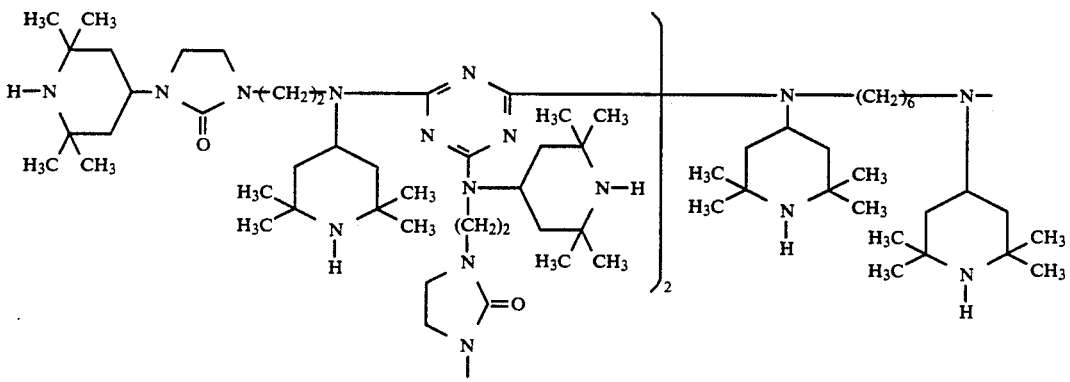

-continued

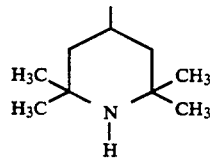

according to claim 1.

9. A composition comprising an organic material susceptible to degradation induced by light, heat and oxidation and an effective stabilising amount of a compound of the formula (I) according to claim 1.

10. A composition according to claim 9, wherein the organic material is a synthetic polymer.

11. A composition according to claim 10, comprising other conventional additives for synthetic polymers in addition to the compounds of the formula (I).

12. A composition according to claim 9, wherein the organic material is a polyolefin.

13. A composition according to claim 9, wherein the organic material is polyethylene or polypropylene.

14. A method for stabilising an organic material against degradation induced by light, heat and oxidation, which comprises incorporating into said organic material an effective stabilising amount of a compound of the formula (I) according to claim 1.

* * * * *